(12) United States Patent
Compton et al.

(10) Patent No.: US 11,834,697 B2
(45) Date of Patent: Dec. 5, 2023

(54) ELECTROCHEMICAL RECOGNITION AND QUANTIFICATION OF CYTOCHROME C OXIDASE EXPRESSION IN BACTERIA

(71) Applicant: OXFORD UNIVERSITY INNOVATION LIMITED, Oxford (GB)

(72) Inventors: Richard Guy Compton, Oxford (GB); Sabine Kuss, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 529 days.

(21) Appl. No.: 16/644,539

(22) PCT Filed: Sep. 17, 2018

(86) PCT No.: PCT/GB2018/052642
§ 371 (c)(1),
(2) Date: Mar. 5, 2020

(87) PCT Pub. No.: WO2019/053467
PCT Pub. Date: Mar. 21, 2019

(65) Prior Publication Data
US 2020/0199644 A1 Jun. 25, 2020

(30) Foreign Application Priority Data
Sep. 15, 2017 (GB) ..................... 1714928

(51) Int. Cl.
*C12Q 1/26* (2006.01)
*C12Q 1/02* (2006.01)
(Continued)

(52) U.S. Cl.
CPC ............... *C12Q 1/26* (2013.01); *C12Q 1/025* (2013.01); *G01N 27/3277* (2013.01);
(Continued)

(58) Field of Classification Search
None
See application file for complete search history.

(56) References Cited

U.S. PATENT DOCUMENTS

| 4,840,893 A | 6/1989 | Hill et al. |
| 5,188,941 A | 2/1993 | Decastro et al. |

(Continued)

FOREIGN PATENT DOCUMENTS

| AU | 580257 B2 | 1/1989 |
| AU | 663869 B2 | 10/1995 |

(Continued)

OTHER PUBLICATIONS

Pellitero et al., "Quantitative self-powered electrochromic biosensors," Chemical Science, vol. 8, pp. 1995-2002 (2017).
(Continued)

*Primary Examiner* — J. Christopher Ball
(74) *Attorney, Agent, or Firm* — Bookoff McAndrews, PLLC

(57) ABSTRACT

A method of determining the presence of bacteria expressing cytochrome c oxidase ('the bacteria'), the method comprising: —providing a sample suspected of containing the bacteria; —providing a compound that has two redox states: a reduced state and an oxidised state, wherein cytochrome c oxidase can convert the compound from its reduced state to its oxidised state; —contacting an electrode either with (i) the compound in its oxidised state in the presence of the sample, then applying a reductive potential and measuring the current at the electrode; or (ii) the compound in its reduced state in the presence of the sample, then applying an oxidative potential and measuring the current at the electrode; and—comparing the magnitude of the current produced by the reductive potential or oxidative potential in the presence of the sample suspected of containing the bacteria with the magnitude of the current produced under the same
(Continued)

conditions, but in the absence of the sample suspected of containing the bacteria, wherein a difference between the magnitude of current produced in the presence of the sample suspected of containing the bacteria and the magnitude of current produced in the absence of the sample suspected of containing the bacteria indicates the presence of the bacteria. Also provided herein is a sensor for determining the presence of bacteria expressing cytochrome c oxidase.

20 Claims, 20 Drawing Sheets

(51) Int. Cl.
*G01N 27/327* (2006.01)
*G01N 27/416* (2006.01)
*G01N 27/48* (2006.01)

(52) U.S. Cl.
CPC ......... *G01N 27/4161* (2013.01); *G01N 27/48* (2013.01); *G01N 2333/90216* (2013.01)

(56) References Cited

U.S. PATENT DOCUMENTS

| | | | |
|---|---|---|---|
| 5,356,786 A | 10/1994 | Heller et al. | |
| 5,489,510 A | 2/1996 | Lopukhin et al. | |
| 6,140,067 A | 10/2000 | Anderson et al. | |
| 6,303,290 B1 | 10/2001 | Liu et al. | |
| 6,340,597 B1 | 1/2002 | Svorc et al. | |
| 6,489,095 B2 | 12/2002 | Herrnstadt et al. | |
| 7,485,212 B2 | 2/2009 | Willner et al. | |
| 7,563,588 B2 | 7/2009 | Gao et al. | |
| 7,842,483 B2 | 11/2010 | Asakura et al. | |
| 8,083,677 B2 | 12/2011 | Rohde | |
| 8,252,606 B2 | 8/2012 | Hulko et al. | |
| 8,304,201 B2 | 11/2012 | Adamczyk et al. | |
| 8,754,051 B2 | 6/2014 | Johnson et al. | |
| 8,758,936 B2 | 6/2014 | Valkiainen et al. | |
| 8,859,151 B2 | 10/2014 | Minteer et al. | |
| 9,540,676 B1 | 1/2017 | Zengler et al. | |
| 9,671,361 B2 | 6/2017 | Kim et al. | |
| 2002/0055127 A1 | 5/2002 | Gindilis | |
| 2004/0014180 A1 | 1/2004 | Bott et al. | |
| 2004/0023293 A1 | 2/2004 | Kreimer et al. | |
| 2004/0092004 A1* | 5/2004 | Stanford, Jr. ............ | C12Q 1/04 435/287.1 |
| 2004/0241205 A1 | 12/2004 | Babich et al. | |
| 2005/0067278 A1 | 3/2005 | Sode | |
| 2006/0188997 A1 | 8/2006 | Abramson et al. | |
| 2006/0222564 A1 | 10/2006 | Dale et al. | |
| 2006/0269826 A1 | 11/2006 | Katz et al. | |
| 2007/0034512 A1 | 2/2007 | Yamaoka et al. | |
| 2007/0105119 A1 | 5/2007 | Gao et al. | |
| 2008/0145313 A1 | 6/2008 | Watson et al. | |
| 2008/0220441 A1 | 9/2008 | Birnbaum et al. | |
| 2008/0280294 A1 | 11/2008 | Petros et al. | |
| 2008/0293101 A1 | 11/2008 | Peters et al. | |
| 2009/0053736 A1 | 2/2009 | Mattingly et al. | |
| 2009/0053747 A1 | 2/2009 | Mattingly et al. | |
| 2009/0054955 A1 | 2/2009 | Kopell et al. | |
| 2009/0226898 A1 | 9/2009 | Sheard | |
| 2010/0004521 A1 | 1/2010 | Epps | |
| 2010/0075393 A1 | 3/2010 | Shear et al. | |
| 2010/0113496 A1 | 5/2010 | Gant | |
| 2010/0120756 A1 | 5/2010 | Gant et al. | |
| 2010/0133117 A1 | 6/2010 | Gao | |
| 2010/0143296 A1 | 6/2010 | Gant | |
| 2010/0160428 A1 | 6/2010 | Cooper et al. | |
| 2010/0270543 A1 | 10/2010 | Choi et al. | |
| 2011/0129818 A1 | 6/2011 | Adamczyk et al. | |
| 2011/0136141 A1 | 6/2011 | Adamczyk et al. | |
| 2011/0136158 A1 | 6/2011 | Takenaka et al. | |
| 2011/0319878 A1 | 12/2011 | Dimauro et al. | |
| 2012/0020972 A1 | 1/2012 | Yoshimura et al. | |
| 2013/0075277 A1 | 3/2013 | Kaneda et al. | |
| 2015/0011630 A1 | 1/2015 | Goldstein et al. | |
| 2015/0050566 A1 | 2/2015 | Ulyanova et al. | |
| 2015/0258171 A1 | 9/2015 | Akerstrom et al. | |
| 2016/0223530 A1 | 8/2016 | Marshall et al. | |
| 2016/0231330 A1 | 8/2016 | Chaves Fontes et al. | |
| 2016/0304929 A1 | 10/2016 | Jiang et al. | |
| 2016/0346297 A1 | 12/2016 | Sheehan | |
| 2017/0105960 A1 | 4/2017 | Elmer et al. | |
| 2017/0218418 A1 | 8/2017 | Douchin et al. | |

FOREIGN PATENT DOCUMENTS

| | | |
|---|---|---|
| AU | 692212 B2 | 6/1998 |
| AU | 692453 B2 | 6/1998 |
| AU | 2002301502 A1 | 3/2003 |
| AU | 2002324317 A1 | 3/2003 |
| AU | 759180 B2 | 4/2003 |
| AU | 2003203980 A1 | 6/2003 |
| AU | 2003265250 A1 | 3/2004 |
| AU | 2004256264 B2 | 1/2005 |
| AU | 2006231498 A1 | 10/2006 |
| AU | 2006292203 A1 | 3/2007 |
| AU | 2006208991 A1 | 5/2007 |
| AU | 2006339607 A1 | 9/2007 |
| AU | 2008230832 A1 | 10/2008 |
| AU | 2012203353 B2 | 6/2012 |
| AU | 201306632 A1 | 7/2013 |
| AU | 2008206486 C1 | 9/2013 |
| AU | 2011326732 B2 | 7/2016 |
| CA | 1223638 A | 6/1987 |
| CA | 1339794 C | 4/1998 |
| CA | 2219040 A1 | 9/1998 |
| CA | 2893245 A2 | 2/2016 |
| CA | 2935144 A2 | 3/2016 |
| CA | 2916374 A1 | 6/2016 |
| CA | 2917336 A1 | 7/2016 |
| CA | 2881746 A1 | 8/2016 |
| CA | 2920246 A1 | 8/2016 |
| CA | 2920272 A2 | 8/2016 |
| CA | 2893402 A1 | 11/2016 |
| CA | 2894005 A1 | 12/2016 |
| CA | 2895743 A1 | 12/2016 |
| EP | 0018825 A1 | 11/1980 |
| EP | 0663446 A2 | 7/1995 |
| EP | 1853916 A2 | 11/2007 |
| EP | 2900254 B1 | 4/2013 |
| EP | 2694667 B1 | 7/2016 |
| EP | 3095868 A2 | 11/2016 |
| EP | 3179869 A1 | 6/2017 |
| EP | 3191040 B1 | 7/2020 |
| WO | WO 98/41648 A3 | 9/1998 |
| WO | WO 00/63441 A3 | 10/2000 |
| WO | WO 01/16373 A3 | 3/2001 |
| WO | WO 03/016500 A3 | 2/2003 |
| WO | WO 2004/037192 A3 | 5/2004 |
| WO | WO 2006/089245 A1 | 8/2006 |
| WO | WO 2007/121246 A3 | 10/2007 |
| WO | WO 2008/097190 A1 | 8/2008 |
| WO | WO 2008/137846 A2 | 11/2008 |
| WO | WO 2010/015260 A2 | 2/2010 |
| WO | WO 2010/040901 A1 | 4/2010 |
| WO | WO 2010/117341 A1 | 10/2010 |
| WO | WO 2011/084540 A1 | 7/2011 |
| WO | WO 2012/061432 A1 | 5/2012 |
| WO | WO 2012/078932 A1 | 6/2012 |
| WO | WO 2013/103780 A2 | 7/2013 |
| WO | WO 2015/155230 A1 | 10/2015 |
| WO | WO 2016/023844 A1 | 2/2016 |
| WO | WO 2016/040534 A1 | 3/2016 |
| WO | WO 2016/189163 A1 | 12/2016 |
| WO | WO 2017/025362 A1 | 2/2017 |

OTHER PUBLICATIONS

Randviir et al., "The fabrication, characterisation and electrochemical investigation of screen-printed graphene electrodes," Physical Chemistry Chemical Physics, vol. 16, pp. 4598-4611 (2014).

(56) References Cited

OTHER PUBLICATIONS

Jurtshuk Jr. et al., "Use of a Quantitative Oxidase Test for Characterizing Oxidative Metabolism in Bacteria," Applied and Environmental Microbiology, vol. 31, No. 5, pp. 668-679 (1976).
Kuss et al., "Electrochemical recognition and quantification of cytochrome c expression in *Bacillus subtilis* and aerobe/anaerobe *Escherichia coli* using N,N,N',N'-tetramethyl-para-phenylene-diamine (TMPD)," Chemical Science, vol. 8, pp. 7682-7688 (2017).
International Search Report in PCT/GB2018/052642, dated Nov. 23, 2018 (4 pages).
Jomma et al., "Recent advances on electrochemical enzyme biosensors," *Current Analytical Chemistry*, vol. 12, pp. 5-21 (2016).
Bergner et al., "Recent advances in high resolution scanning electrochemical microscopy of living cells—A review," Analytica Chimica Acta, vol. 775, pp. 1-13 (2013).
Li et al., "Quantitative Chemical Measurements of Vesicular Transmitters with Electrochemical Cytometry," Accounts of Chemical Research, vol. 49, pp. 2347-2354 (2016).
Yakushenko et al., "Parallel On-Chip Analysis of Single Vesicle Neurotransmitter Release," Analytical Chemistry, vol. 85, pp. 5483-5490 (2013).
Michaelis et al., "The Free Radicals of the Type of Wurster's Salts," *Journal of the American Chemical Society*, vol. 61, 1981-1992 (1939).
Menshykau et al., "Influence of electrode roughness on cyclic voltammetry," *The Journal of Physical Chemistry C.*, vol. 112, pp. 14428-14438 (2008).
Gordon et al., "The practical application of the direct oxidase reaction in bacteriology," The Journal of Pathology and Bacteriology, vol. 31, pp. 185-190 (1928).
Rudolph, M., "A fast implicit finite difference algorithm for the digital simulation of electrochemical processes," *Journal of Electroanalytical Chemistry*, vol. 314, pp. 13-22 (1991).
Rudolph, M., "Digital simulations with the fast implicit finite difference (FIFD) algorithm: Part II. An improved treatment of electrochemical mechanisms with second-order reactions," *Journal of Electroanalytical Chemistry*, vol. 338, pp. 85-98 (1992).
Rudolph, M., "Digital simulations with the fast implicit finite-difference (FIFD) algorithm. part 4. Simulation of electrical migration and diffuse double-layer effects," *Journal of Electroanalytical Chemistry*, vol. 375, pp. 89-99 (1994).
Rudolph et al., "A Simulator for Cyclic Voltammetric Responses," *Analytical Chemistry*, vol. 66, No. 10, pp. 589A-600A (1994).
Fisher et al., "Nonradioactive Assay for Cellular Dimethylallyl Diphosphate," *Analytical Biochemistry*, vol. 292, pp. 272-279 (2001).
Cardwell et al., "Preparation of Microelectrodes: Comparison of Polishing Procedures by Statistical Analysis of Voltammetric Data," Analyst, vol. 121, pp. 357-362 (1996).
Berezin et al., "Use of cytochrome c oxidase in a regenerative oxygen electrode", Bioorganicheskaya Khimiya, vol. 3., Abstract, 1977 (1 page).
Groom et al., "Dual Functionalities of 4-Aminophenylamine in Enzymatic Assay and Mediated Biosensor Construction," *Analytical Biochemistry*, vol. 231, pp. 393-399 (1995).
Maalouf et al., "Label-Free Detection of Bacteria by Electrochemical Impedance Spectroscopy: Comparison to Surface Plasmon Resonance," *Analytical Chemistry*, vol. 79, No. 13, pp. 4879-4886 (2007).
Kuss et al., "Electrocatalytic detection of ascorbic acid using N,N,N',N'-tetramethyl-para-phenylene-diamine (TMPD) mediated oxidation at unmodified gold electrodes; reaction mechanism and analytical application," Electrochimica Acta vol. 242, pp. 19-24 (2017).
Wang et al., "Polyhydroquinone-graphene composite as new redox species for sensitive electrochemical detection of cytokeratins antigen 21-1," Scientific Reports, vol. 6, No. 30623, pp. 1-6 (2016).
Adams et al., "In vitro electrochemistry of biological systems," Annual Review of Analytical Chemistry, vol. 1, pp. 1-23 (2008).
Ivnitski et al., "Application of Electrochemical Biosensors for Detection of Food Pathogenic Bacteria," Electroanalysis, vol. 12, No. 5, pp. 317-325 (2000).
Batchelor-Mcauley et al., "In Situ Nanoparticle Sizing with Zeptomole Sensitivity," The Analyst, vol. 140, pp. 1-17 (2015).
Yang et al., "Electrical/electrochemical impedance for rapid detection of foodborne pathogenic bacteria," Biotechnology Advances, vol. 26, pp. 135-150 (2008).
Bard et al., "Chemically imaging living cells by scanning electrochemical microscopy," Biosensors and Bioelectronics, vol. 22, pp. 461-472 (2006).
Nebel et al., "Visualization of Oxygen Consumption of Single Living Cells by Scanning Electrochemical Microscopy: The influence of the Faradaic Tip Reaction," Angewandte Chemie International Edition, vol. 52 pp. 6335-6338 (2013).
Kuss et al., "Assessment of multidrug resistance on cell coculture patterns using scanning electrochemical microscopy," PNAS, vol. 110, pp. 9249-9254 (2013).
Chan et al., "Catalytic activity of catalase-silica nanoparticle hybrids: from ensemble to individual entity activity," *Chemical Science*, vol. 8, pp. 2303-2308 (2017).
Nobre et al., "The oxidase test in yeasts of medical importance," Journal of Medical Microbiology, vol. 23 pp. 359-361 (1987).
Tenaillon et al., "The population genetics of commensal *Escherichia coli*," Nature Reviews Microbiology, vol. 8, pp. 207-217 (2010).
Yamauchi et al., "Magnetic Study of N,N,N', N'-tetramethyl-phenylene diamine (Wurster's Blue) Iodide Cation Radical," *Bulletin of the Chemical Society of Japan*, vol. 63, pp. 2928-2932 (1990).
Thöny-Meyer et al., "*Escherichia coli* Genes Required for Cytochrome c Maturation," Journal of Bacteriology, vol. 177, No. 15, pp. 4321-4326 (1995).
Iobbi-Nivol et al., "A reassessment of the range of c-type cytochromes synthesized by *Escherichia coli* K-12", FEMS Microbiology Letters, vol. 119, pp. 89-94 (1994).
Chang et al., "Oxygen Deprivation Triggers Upregulation of Early Growth Response-1 by the Receptor for Advanced Glycation End Products," *Circulation Research*, vol. 102, pp. 905-913 (2008).
Von Wachenfeldt et al., "*Bacillus subtilis* holo-cytochrome c-550 can be synthesised in aerobic *Escherichia coli*," FEBS Letters, vol. 270, pp. 147-151 (1990).
Agilent Technologies, "*E.coli* Cell Culture Concentration from OD600", (2017). http://www.genomics.agilent.com/biocalculators/calcODBacterial.jsp (1 page).
Arrieta et al., "Antimicrobial activity in the egg wax of the African cattle tick *Amblyomma hebraeum* (Acari: Ixodidae)," Department of Biological Sciences, University of Alberta, 2006 (36 pages).

\* cited by examiner

ELECTROCHEMICAL RECOGNITION AND QUANTIFICATION OF CYTOCHROME C OXIDASE EXPRESSION IN BACTERIA

CROSS-REFERENCE TO RELATED APPLICATIONS

This application is a U.S. national stage filing under 35 U.S.C. § 371 of International Application No. PCT/GB2018/052642, filed on Sep. 17, 2018, which claims benefit of priority to GB Application No. 1714928.7, filed on Sep. 15, 2017.

FIELD OF THE INVENTION

The present invention relates to an electrochemical method for determining the presence of bacteria expressing cytochrome c oxidase in a sample and/or quantifying the enzymatic production of cytochrome c oxidase.

BACKGROUND

The oxidase test is a microbiological test used to determine if bacteria express cytochrome c oxidase, as well as whether a sample contains bacteria that are known to express cytochrome c oxidase. In the oxidase test, a compound having two redox states, usually N,N,N',N'-tetramethyl-para-phenylene diamine (TMPD) or N,N-dimethyl-para-phenylene diamine (DMPD; optionally, in the presence of alpha-naphthol), is used as an artificial electron donor for cytochrome c oxidase. When a bacteria expressing cytochrome c oxidase is present, the compound is oxidised by cytochrome c oxidase and converted from its colourless reduced state to the dark-blue coloured oxidised state.

However, this colorimetric test has low sensitivity due to its reliance on a visible colour change. Moreover, although the oxidase test provides a qualitative indication of the presence of bacteria expressing cytochrome c oxidase, the test cannot provide any quantitative data.

BRIEF DESCRIPTION OF THE FIGURES

The Figures illustrate results from the Examples below. FIGS. 9 to 20 relate to Example 2.

FIG. 1 shows cyclic voltammograms of 1 mM TMPD and TMPD-BF$_4$ using a 6.9 μm diameter gold electrode in PBS at pH 7.4.

FIG. 2 shows an electrochemical analysis of TMPD-BF$_4$ by cyclic voltammetry. a) Experimental (full lines) and simulated (dotted lines) cyclic voltammograms in 2.1 mM TMPD-BF$_4$. b) Linear relationship of the reductive peak current and square root of scan rate (V) for both experimental and simulation data.

FIG. 3 is a schematic representation of the electrochemical recognition of the presence of bacteria expressing cytochrome c oxidase. The immobilization of bacteria onto a 3 mm gold electrode by drop-casting results in the local oxidation of TMPD to TMPD$^{+•}$ by bacterial cytochrome c oxidases. TMPD$^{+•}$ can be converted to TMPD at the electroactive surface of the electrode, resulting in an increase in the magnitude of the reduction current during cyclic voltammetry or chronoamperometry.

FIG. 4 shows the electrochemical analysis of B. subtilis in 1.7 mM TMPD-BF$_4$. a) B. subtilis oxidase test positive bacteria (inset test tube left) result in an increase in the magnitude of the electrochemical current until a surface concentration of 2.5 monolayers (ML) is reached. b) B. subtilis oxidase test negative bacteria (inset test tube right) function as a negative control. Error bar represents three times the standard deviation.

FIG. 5 shows the electrochemical analysis of B. subtilis and E. coli by chronoamperometry. a) E. coli oxidase test negative bacteria (inset) result in an increase in current in the presence of TMPD$^{+•}$ at various monolayer (ML) concentrations. Error bar represents three times the standard deviation. b) Chronoamperometry in 0.5 mM TMPD-BF$_4$ in the presence of 3×10$^7$ E. coli bacteria (equivalent of 3 ML), drop-cast onto a 3 mm gold electrode surface. Different delay times have been applied, resulting in a maximum current response at a delay time of 45 s before measurement is performed. c) Normalized current difference between controls (unmodified electrode) and samples containing B. subtilis and E. coli bacteria, grown under different culture conditions. A linear relationship can be seen for currents of samples containing up to 1×10$^7$ immobilized cells.

FIG. 6 shows results of chronoamperometry of 2.0 mM TMPD-BF$_4$ in the presence of different concentrations of E. coli bacteria (grown to stationary phase), drop-cast onto a 3 mm (diameter) gold electrode surface.

FIG. 7 shows results of flow cytometry measurements, revealing information about cell viability in solution.

FIG. 8 shows results of cyclic voltammetry for 0.5 mM TMPD-BF$_4$ in PBS (full lines) in the presence (grey) and the absence (black) of E. coli bacteria, drop-cast onto a 3 mm gold electrode. Dotted lines represent cyclic voltammetry in PBS (pH 7.4) only. The consumption of oxygen by the bacteria can be seen in the reduced reduction signal in PBS and an increase in TMPD reduction was observed.

FIG. 9A shows a bare gold substrate compared to FIG. 9B, which shows a fully functionalized gold surface with immobilized E. coli bacteria; FIG. 9C shows an unmodified gold substrate on an SPE (Zimmer&Peacock) compared to FIGS. 9D and 9E, which show a functionalized SPE, showing the immobilization of biotinylated fluorescent beads.

FIG. 10 shows a schematic representation of surface modifications of a gold electrode, in particular, it shows: self-assembled monolayers of biotinylated thiols, capped with BSA, allows binding of neutravidin, with affinity to a biotinylated antibody, which captures target bacteria.

FIG. 11 shows the detection of E. coli at functionalized macroelectrodes. An electrochemical current increase is observed following the binding of E. coli to a fully functionalized macroelectrode (grey), compared to a bare electrode (black). The error bar is representing three times the standard deviation.

FIG. 12 shows a negative control at a functionalized macroelectrode. No increase in electrochemical current is observed at the electrode in the absence of E. coli bacteria (dotted line), compared to a bare electrode (full line). Error bars are representing three times the standard deviation.

FIG. 13 shows the detection of A. faecalis at a macroelectrodes. Dropcasted A. faecalis are detected at a macroelectrode, as the electrochemical current increases significantly (grey). Error bars are representing three times the standard deviation.

FIG. 14 shows a negative control in the presence of A. faecalis at a macroelectrodes. The exposure of A. faecalis to a fully functionalized macroelectrode, containing an anti-E. coli antibody does not result in an increase of the electrochemical current (grey), which cannot be distinguished from the signal obtained at control electrodes (black=bare electrode, dark grey=modified electrode in the absence of bacteria). Error bars are representing three times the standard deviation.

FIG. 15 shows the electrochemistry of TMPD at SPEs provided by Zimmer&Peacock.

FIG. 16 shows the detection of *N. gonorrhoea* at functionalized SPEs, containing an anti-*N. gonorrhoea* antibody. Immobilized *N. gonorrhoea* bacteria result in a significantly enhanced electrochemical current (grey), in contrast to a blank electrode (black, full line) and a functionalized sensor, in the absence of bacteria (black, dotted line). Error bars are representing three times the standard deviation.

FIG. 17 shows the detection of *E. coli* at functionalized SPEs containing an anti-*E. coli* antibody. Immobilized *E. coli* bacteria result in a significantly enhanced electrochemical current (grey), in contrast to the control, in the absence of bacteria (black). Error bars are representing three times the standard deviation.

FIG. 18 shows PBS control experiment for a single functionalized SPEs containing an anti-*E. coli* antibody. No significant change in current is observed after a 1 hour incubation of the sensor in PBS. Error bars are representing three times the standard deviation.

FIG. 19 shows the detection of *E. coli* at single functionalized SPEs containing an anti-*E. coli* antibody. Controls showing fully functionalized sensors before incubation with bacteria (black lines). After one hour of sensor incubation in bacteria suspension, immobilized *E. coli* bacteria result in a significantly enhanced electrochemical current (grey lines). Error bars are representing three times the standard deviation.

FIG. 20 shows the detection of *E. coli* at functionalized SPEs containing an anti-*E. coli* antibody at different concentrations. Immobilized *E. coli* bacteria result in a significantly enhanced electrochemical current, in contrast to the control, in the absence of bacteria (dotted line). Error bars are representing three times the standard deviation.

SUMMARY OF THE INVENTION

Figure 1:
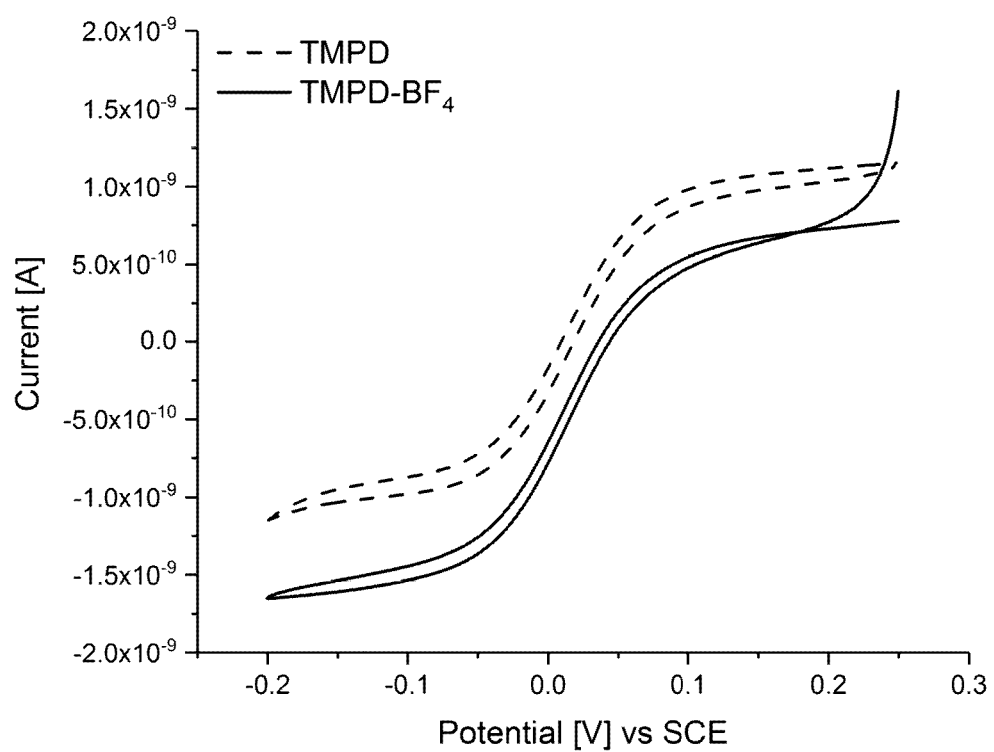
FIGS. 1 to 8 relate to Example 1.

In a first aspect, there is provided a method of determining the presence of bacteria expressing cytochrome c oxidase ('the bacteria'), the method comprising:
providing a sample suspected of containing the bacteria;
providing a compound that has two redox states: a reduced state and an oxidised state, wherein cytochrome c oxidase can convert the compound from its reduced state to its oxidised state;
contacting an electrode either with
(i) the compound in its oxidised state in the presence of the sample, then applying a reductive potential and measuring the current at the electrode; or
(ii) the compound in its reduced state in the presence of the sample, then applying an oxidative potential and measuring the current at the electrode;
and
comparing the magnitude of the current produced by the reductive potential or oxidative potential in the presence of the sample suspected of containing the bacteria with the magnitude of the current produced under the same conditions, but in the absence of the sample suspected of containing the bacteria,
wherein a difference between the magnitude of current produced in the presence of the sample suspected of containing the bacteria and the magnitude of current produced in the absence of the sample suspected of containing the bacteria indicates the presence of the bacteria.

In a second aspect, there is provided an electrochemical sensor for determining the presence of bacteria expressing cytochrome c oxidase ('the bacteria') in a sample suspected of containing the bacteria, the sensor comprising:
an electrode; and
a compound that has two redox states: a reduced state and an oxidised state, wherein cytochrome c oxidase can convert the compound from its reduced state to its oxidised state; and
the sensor is adapted to:
contact the electrode with a sample suspected of containing the bacteria and either with
(i) the compound in its oxidised state, then apply a reductive potential and measure the current at the electrode; or
(ii) the compound in its reduced state, then apply an oxidative potential and measure the current at the electrode; and
compare the magnitude of the current produced by the reductive potential or oxidative potential in the presence of the sample suspected of containing the bacteria with the magnitude of the current produced under the same conditions, but in the absence of the sample suspected of containing the bacteria,
wherein a difference between the magnitude of current produced in the presence of the sample suspected of containing the bacteria and the magnitude of current produced in the absence of the sample suspected of containing the bacteria indicates the presence of the bacteria.

The present inventors have found a method for the electrochemical recognition of the oxidase test, by means of cytochrome c oxidase detection, and its quantitative analysis, expressed as a turnover number, calculated for single bacteria. The oxidation of certain compounds, for example, TMPD, by bacterial oxidases, specifically cytochrome c oxidase, a transmembrane protein that plays an important role as an electron acceptor in the respiratory electron transport chain, has been successfully monitored in bacteria, for example, *Bacillus subtilis* (*B. subtilis*) and *Escherichia coli* (*E. coli*). This represents the first time cytochrome c oxidase expression has been measured in aerobically grown *E. coli*, demonstrating the capabilities of electrochemistry applied to biological samples. *E. coli* are gram negative, rod-shaped bacteria, representing an ideal model organism for many studies in molecular biology because of its high proliferation rate in growth medium in laboratory culture flasks. Being part of the normal gut flora in many vertebrates, but also being responsible for about 2 million deaths per year, related to intraintestinal and extraintestinal diseases, *E. coli* is known for both its commensalism and pathogenicity. In contrast to other gram-negative bacteria, *E. coli* is a facultative anaerobic organism that, if grown in the presence of oxygen, cannot be detected by the colorimetric oxidase test. The present inventors have demonstrated the ability of electrochemistry to detect trace amounts of electrochemically active substances and provides an accurate, fast and inexpensive analytical method for pathogenic and non-pathogenic bacteria, based on electroactive species converted by the organisms.

DETAILED DESCRIPTION

The present invention provides the aspects mentioned above. Optional and preferred features of the various aspects are described below. Unless otherwise stated, any optional or preferred feature may be combined with any other optional or preferred feature, and with any of the aspects of the invention mentioned herein.

The method of determining the presence of bacteria expressing cytochrome c oxidase ('the bacteria') involves
providing a sample suspected of containing the bacteria;
providing a compound that has two redox states: a reduced state and an oxidised state, wherein cytochrome c oxidase can convert the compound from its reduced state to its oxidised state;
contacting an electrode either with
(i) the compound in its oxidised state in the presence of the sample, then applying a reductive potential and measuring the current at the electrode; or
(ii) the compound in its reduced state in the presence of the sample, then applying an oxidative potential and measuring the current at the electrode; and
comparing the magnitude of the current produced by the reductive potential or oxidative potential in the presence of the sample suspected of containing the bacteria with the magnitude of the current produced under the same conditions, but in the absence of the sample suspected of containing the bacteria,
wherein a difference between the magnitude of current produced in the presence of the sample suspected of containing the bacteria and the magnitude of current produced in the absence of the sample suspected of containing the bacteria indicates the presence of the bacteria.

The current may be measured by any suitable electrochemical technique. Optionally, the current is measured by cyclic voltammetry or chronoamperometry. The voltammetry or chronoamperometry experiment may be carried out using a suitable electrochemical analytical device, for example, a potentiostat.

In (i), the reductive potential should be of a sufficient magnitude to reduce the compound from its oxidised state to its reduced state. In an embodiment, the reductive potential may be −1 V or more (i.e. more positive), optionally −0.9 V or more, optionally −0.8 V or more, optionally −0.0.7 V or more, optionally −0.6 V or more, optionally −0.5 V or more, optionally −0.4 V or more, optionally −0.3 V or more, optionally −0.2 V or more.

In (i), the reductive potential may be −100 mV or less, in some examples, −110 mV or less, in some examples, −120 mV or less, in some examples, −130 mV or less, in some examples, −140 mV or less, in some examples, −150 mV or less, in some examples, −160 mV or less, in some examples, −170 mV or less, in some examples, −180 mV or less, in some examples, −190 mV or less, in some examples, about −200 mV. In (i), the reductive potential may be −200 mV or more, in some examples, −190 mV or more, in some examples, −180 mV or more, in some examples, −170 mV or more, in some examples, −160 mV or more, in some examples, −150 mV or more, in some examples, −140 mV or more, in some examples, −130 mV or more, in some examples, −120 mV or more, in some examples, −110 mV or more, in some examples, about −100 mV. In (i), the reductive potential may be −100 mV to −200 mV, in some examples, −110 mV to −190 mV, in some examples, −120 mV to −180 mV, in some examples, −130 mV to −170 mV, in some examples, −140 mV to −160 mV, in some examples, −150 mV to −160 mV, in some examples, −140 mV to −150 mV. The potentials given in this paragraph may be suitable for the use of TMPD and some variants thereof as the compound. All potentials given herein, unless otherwise stated, are indicated vs saturated calomel electrode (i.e. vs SCE).

In (i), the reductive potential may be applied for 1 s or more, in some examples, 2 s or more, in some examples, 3 s or more, in some examples, 4 s or more, in some examples, 5 s or more, in some examples, 6 s or more, in some examples, 7 s or more, in some examples, 8 s or more, in some examples, 9 s or more, in some examples, about 10 s. In (i), the reductive potential may be applied for 10 s or less, in some examples, 9 s or less, in some examples, 8 s or less, in some examples, 7 s or less, in some examples, 6 s or less, in some examples, 5 s or less, in some examples, 4 s or less, in some examples, 3 s or less, in some examples, 2 s or less, in some examples, about 1 s. In (i), the reductive potential may be applied for 1 s to 10 s, in some examples, 2 s to 9 s, in some examples, 3 s to 8 s, in some examples, 4 s to 7 s, in some examples, 5 s to 6 s.

In (ii), the oxidative potential should be of a sufficient magnitude to oxidise the compound from its reduced state to its oxidised state. In an embodiment, the oxidative potential may be 1 V or less (i.e. less positive), optionally 0.9 V or less, optionally 0.8 V or less, optionally 0.7 V or less, optionally 0.6 V or less, optionally 0.5 V or less, optionally 0.4 V or less, optionally 0.3 V or less, optionally 0.2 V or less.

In (ii), the oxidative potential may be 100 mV or more, in some examples, 110 mV or more, in some examples, 120 mV or more, in some examples, 130 mV or more, in some examples, 140 mV or more, in some examples, 150 mV or more, in some examples, 160 mV or more, in some examples, 170 mV or more, in some examples, 180 mV or more, in some examples, 190 mV or more, in some examples, about 200 mV. In (ii), the oxidative potential may be 200 mV or less, in some examples, 190 mV or less, in some examples, 180 mV or less, in some examples, 170 mV or less, in some examples, 160 mV or less, in some examples, 150 mV or less, in some examples, 140 mV or less, in some examples, 130 mV or less, in some examples, 120 mV or less, in some examples, 110 mV or less, in some examples, about 100 mV. In (ii), the oxidative potential may be 100 mV to 200 mV, in some examples, 110 mV to 190 mV, in some examples, 120 mV to 180 mV, in some examples, 130 mV to 170 mV, in some examples, 140 mV to 160 mV, in some examples, 150 mV to 160 mV, in some examples, 140 mV to 150 mV.

In (ii), the oxidative potential may be applied for 1 s (second) or more, in some examples, 2 s or more, in some examples, 3 s or more, in some examples, 4 s or more, in some examples, 5 s or more, in some examples, 6 s or more, in some examples, 7 s or more, in some examples, 8 s or more, in some examples, 9 s or more, in some examples, 10 s or more, in some examples 30 s or more, in some examples 1 minute or more, in some examples 2 minutes or more, in some examples 5 minutes or more. In (ii), the oxidative potential may be applied for 10 minutes or less, in some examples 7 minutes or less, in some examples 5 minutes or less, in some examples 3 minutes or less, in some examples, 2 minutes or less, in some examples 1 minute or less, in some examples 30 s or less, in some examples 10 s or less, in some examples, 9 s or less, in some examples, 8 s or less, in some examples, 7 s or less, in some examples, 6 s or less, in some examples, 5 s or less, in some examples, 4 s or less, in some examples, 3 s or less, in some examples, 2 s or less, in some examples, about 1 s. In (ii), the oxidative potential may be applied for 1 s to 10 s, in some examples, 2 s to 9 s, in some examples, 3 s to 8 s, in some examples, 4 s to 7 s, in some examples, 5 s to 6 s.

Optionally, the compound is provided as a mixture of the compound in the oxidised state and the compound in the reduced state. If the compound is provided as a mixture of the compound in the oxidised state and the compound in the reduced state (i) involves, before applying the reductive potential, applying an oxidative potential to convert at least some of, optionally all of, the compound in its reduced state to the compound in its oxidised state; and (ii) involves, before applying the oxidative potential, applying a reductive potential to convert at least some of, optionally all of, the compound in its oxidised state to the compound in its reduced state. In some examples, converting all of the compound in (i) its reduced state to its oxidised state or (ii) its oxidised state to its reduced state means converting all of the compound within the diffusion layer of the electrode from (i) its reduced state to its oxidised state or (ii) its oxidised state to its reduced state.

In (i) the oxidative potential may exceed, optionally significantly exceed, the standard potential of the compound. In (i), the oxidative potential may be 200 mV or more, in some examples, 210 mV or more, in some examples, 220 mV or more, in some examples, 230 mV or more, in some examples, 240 mV or more, in some examples, 250 mV or more, in some examples, 260 mV or more, in some examples, 270 mV or more, in some examples, 280 mV or more, in some examples, 290 mV or more, in some examples 300 mV, in some examples 400 mV or more, in some examples 500 mV or more, in some examples, 500 mV or more, in some examples 600 mV or more, in some examples 700 mV or more, in some examples 800 mV or more, in some examples 900 mV or more. In (i), the oxidative potential may be 1000 mV or less, in some examples 900 mV or less, in some examples 800 mV or less, in some examples 700 mV or less, in some examples 600 mV or less, in some examples 500 mV or less, in some examples 400 mV or less, 300 mV or less, in some examples, 290 mV or less, in some examples, 280 mV or less, in some examples, 270 mV or less, in some examples, 260 mV or less, in some examples, 250 mV or less, in some examples, 240 mV or less, in some examples, 230 mV or less, in some examples, 220 mV or less, in some examples, 210 mV or less, in some examples, about 200 mV. In (i), the oxidative potential may be 200 mV to 300 mV, in some examples, 210 mV to 290 mV, in some examples, 220 mV to 280 mV, in some examples, 230 mV to 270 mV, in some examples, 240 mV to 260 mV, in some examples, 250 mV to 260 mV, in some examples, 240 mV to 250 mV.

In (i), the oxidative potential may be applied for 1 s or more, in some examples, 2 s or more, in some examples, 3 s or more, in some examples, 4 s or more, in some examples, 5 s or more, in some examples, 6 s or more, in some examples, 7 s or more, in some examples, 8 s or more, in some examples, 9 s or more, in some examples, 10 s or more, in some examples 30 s or more, in some examples 1 minute or more, in some examples 2 minutes or more, in some examples 5 minutes or more. In (i), the oxidative potential may be applied for 10 minutes or less, in some examples 7 minutes or less, in some examples 5 minutes or less, in some examples 3 minutes or less, in some examples, 2 minutes or less, in some examples 1 minute or less, in some examples 30 s or less, in some examples 10 s or less, in some examples, 9 s or less, in some examples, 8 s or less, in some examples, 7 s or less, in some examples, 6 s or less, in some examples, 5 s or less, in some examples, 4 s or less, in some examples, 3 s or less, in some examples, 2 s or less, in some examples, about 1 s. In (i), the oxidative potential may be applied for 1 s to 10 s, in some examples, 2 s to 9 s, in some examples, 3 s to 8 s, in some examples, 4 s to 7 s, in some examples, 5 s to 6 s.

In (ii), the magnitude of the reductive potential may exceed, optionally significantly exceed, the magnitude of the standard potential of the compound. In (ii), the reductive potential may be −200 mV or less, in some examples, −210 mV or less, in some examples, −220 mV or less, in some examples, −230 mV or less, in some examples, −240 mV or less, in some examples, −250 mV or less, in some examples, −260 mV or less, in some examples, −270 mV or less, in some examples, −280 mV or less, in some examples, −290 mV or less, in some examples, −300 mV or less, in some examples −400 mV or less, in some examples −500 mV or less, in some examples, −500 mV or less, in some examples −600 mV or less, in some examples 700 mV or less, in some examples 800 mV or less, in some examples 900 mV or less. In (ii), the reductive potential may be −1000 mV or more, in some examples −900 mV or more, in some examples −800 mV or more, in some examples −700 mV or more, in some examples −600 mV or more, in some examples −500 mV or more, in some examples −400 mV or more −300 mV or more, in some examples, −290 mV or more, in some examples, −280 mV or more, in some examples, −270 mV or more, in some examples, −260 mV or more, in some examples, −250 mV or more, in some examples, −240 mV or more, in some examples, −230 mV or more, in some examples, −220 mV or more, in some examples, −210 mV or more, in some examples, about −200 mV. In (ii), the reductive potential may be −200 mV to −300 mV, in some examples, −210 mV to −290 mV, in some examples, −220 mV to −280 mV, in some examples, −230 mV to −270 mV, in some examples, −240 mV to −260 mV, in some examples, −250 mV to −260 mV, in some examples, −240 mV to −250 mV.

In (ii), the reductive potential may be applied for 1 s or more, in some examples, 2 s or more, in some examples, 3 s or more, in some examples, 4 s or more, in some examples, 5 s or more, in some examples, 6 s or more, in some examples, 7 s or more, in some examples, 8 s or more, in some examples, 9 s or more, in some examples, about 10 s or more, in some examples 30 s or more, in some examples 1 minute or more, in some examples 2 minutes or more, in some examples 5 minutes or more. In (ii), the reductive potential may be applied for 10 minutes or less, in some examples 7 minutes or less, in some examples 5 minutes or less, in some examples 3 minutes or less, in some examples, 2 minutes or less, in some examples 1 minute or less, in some examples 30 s or less, in some examples 10 s or less, in some examples, 9 s or less, in some examples, 8 s or less, in some examples, 7 s or less, in some examples, 6 s or less, in some examples, 5 s or less, in some examples, 4 s or less, in some examples, 3 s or less, in some examples, 2 s or less, in some examples, about 1 s. In (ii), the reductive potential may be applied for 1 s to 10 s, in some examples, 2 s to 9 s, in some examples, 3 s to 8 s, in some examples, 4 s to 7 s, in some examples, 5 s to 6 s.

The method may be performed by maintaining the sample suspected of containing the bacteria at a temperature suitable for maintaining bacteria life throughout the method. The temperature suitable for maintaining bacteria life may be between 0° C. and 45° C., in some examples, 5° C. and 45° C., in some examples, 10° C. and 40° C., in some examples, 15° C. and 40° C., in some examples, 20° C. and 45° C., in some examples, 25° C. to 44° C., in some examples, 27° C. to 43° C., in some examples, 30° C. to 43° C., in some examples, 31° C. to 42° C., in some examples, 32° C. to 41° C., in some examples, 33° C. to 40° C., in some examples, 34° C. to 40° C., in some examples, 35° C. to 39° C., in some example, 36° C. to 38° C., in some examples, 36° C. to 37° C. The temperature suitable for maintaining bacteria life may be 37° C.

The method of determining the presence of bacteria expressing cytochrome c oxidase ('the bacteria') may involve
providing a sample suspected of containing the bacteria;
providing a compound that has two redox states: a reduced state and an oxidised state, wherein cytochrome c oxidase can convert the compound from its reduced state to its oxidised state;
contacting an electrode with the compound in its oxidised state in the presence of the sample, then applying a reductive potential and measuring the current at the electrode;
comparing the magnitude of the current produced by the reductive potential in the presence of the sample suspected of containing the bacteria with the magnitude of the current produced under the same conditions, but in the absence of the sample suspected of containing the bacteria,
wherein a higher magnitude of current produced in the presence of the sample suspected of containing the bacteria than the magnitude of current produced in the absence of the sample suspected of containing the bacteria indicates the presence of the bacteria.

The method of determining the presence of bacteria expressing cytochrome c oxidase ('the bacteria') may involve
providing a sample suspected of containing the bacteria;
providing a compound that has two redox states: a reduced state and an oxidised state, wherein cytochrome c oxidase can convert the compound from its reduced state to its oxidised state;
contacting an electrode with the compound in its reduced state in the presence of the sample, then applying an oxidative potential and measuring the current at the electrode; and
comparing the magnitude of the current produced by the oxidative potential in the presence of the sample suspected of containing the bacteria with the magnitude of the current produced under the same conditions, but in the absence of the sample suspected of containing the bacteria,
wherein a lower magnitude of current produced in the presence of the sample suspected of containing the bacteria than the magnitude of current produced in the absence of the sample suspected of containing the bacteria indicates the presence of the bacteria.

Sample Suspected of Containing the Bacteria

The sample suspected of containing a bacteria expressing cytochrome c oxidase may be a sample suspected of containing any bacteria expressing cytochrome c oxidase. The sample suspected of containing a bacteria expressing cytochrome c oxidase may be a sample that contains a bacteria expressing cytochrome c oxidase.

The bacteria may be selected from any gram positive bacteria and gram negative bacteria. The bacteria may be, but are not limited to, a bacteria selected from *Bacillus* bacteria, *Neisseria* bacteria, Pseudomonadaceae bacteria, *Campylobacter* bacteria, *Pasteurella* bacteria, *Alcaligens* bacteria, *Aeromonas* bacteria, *Vibrio* bacteria, *Brucella* bacteria, *Helicobacter* bacteria, *Haemophilus* bacteria, *Moraxella* bacteria, *Legionella pneumophila* bacteria, *Chlamydia trachomatis* bacteria, *Streptococcus* bacteria, *Staphylococcus* bacteria, *Listeria* bacteria, *Mycobacterium tuberculosis* bacteria *Escherichia coli* bacteria and *Alcaligenes* bacteria. The *Bacillus* bacteria may be *Bacillus subtilis*, optionally, *Bacillus subtilis* (strain PY79). The *Neisseria* bacteria may be *Neisseria meningitidis* bacteria or *Neisseria gonorrhoeae* bacteria. The Pseudomonadaceae bacteria may be *Pseudomonas* bacteria, for example, *Pseudomonas aeruginosa* or *Pseudomonas stutzeri*. The *Campylobacter* bacteria may be *Campylobacter jejuni* bacteria. The *Vibrio* bacteria may be *Vibrio cholerae* bacteria. The *Helicobacter* bacteria may be *Helicobacter pylori* bacteria. In some examples, the bacteria may be *Escherichia coli* bacteria. In some examples, the bacteria may be bacteria related to sexually transmitted diseases or infections, for example, *Neisseria gonorrhoeae* and *Chlamydia trachomatis*. The *Alcaligenes* bacteria may be *Alcaligenes faecalis*.

The sample suspected of containing a bacteria expressing cytochrome c oxidase may be or comprise a biomaterial, for example, a biofluid, which may have been drawn from an animal or a plant. The sample suspected of containing the bacteria expressing cytochrome c oxidase may be or comprise a biomaterial, for example, a biofluid, which may have been drawn from a human. The sample suspected of containing a bacteria expressing cytochrome c oxidase may be a liquid sample. Optionally, the sample suspected of containing a bacteria expressing cytochrome c oxidase is a biological sample, which may be selected from a sweat sample, a blood sample, saliva and a urine sample. The blood sample suspected of containing a bacteria expressing cytochrome c oxidase may be selected from a whole blood sample, a plasma sample and a serum sample.

The sample suspected of containing the bacteria may be diluted, for example, in a carrier medium. The carrier medium may be a liquid carrier medium. The carrier medium may be the same as or miscible with the carrier medium in which the compound is placed.

The sample suspected of containing the bacteria may be immobilised on a surface of the electrode. The sample suspected of containing the bacteria may be immobilised on the surface of the electrode by spin-coating, spray-coating, dip-coating, drop-casting, printing (for example, inkjet printing, flexographic printing or gravure printing) or application by syringe. The sample suspected of containing the bacteria may be immobilised on the surface of the electrode by drop-casting.

The sample suspected of containing the bacteria may be grown on a surface of the electrode, i.e the sample may be placed on the electrode and the bacteria in the sample allowed to grow.

In an embodiment, the bacteria may be immobilized by attachment to the surface of the electrode by a species selective for the bacteria, for example, a species selected from an antibody, an antibody fragment, an aptamer and a bacteriophage (e.g. a T4 bacteriophage). The antibody may be selected from a monoclonal antibody or a polyclonal antibody. These may allow the limit of detection to be lowered compared to non-selective electrodes, and, because of the selectivity, allow it to be determined if certain bacteria are present in a sample (with only those for which the electrode is selective adhering to the electrode after exposure to the sample).

The sample suspected of containing the bacteria may be contacted with the electrode, the compound and/or the carrier medium for any length of time (referred to in the Examples as a delay time) before the current is measured, for example, for 3 minutes or less before the current is measured. The sample suspected of containing the bacteria may be contacted with the electrode, the compound and/or the carrier medium immediately before the current is measured. The sample suspected of containing the bacteria may be contacted with the electrode, the compound and/or the carrier medium 120 s or less, in some examples, 110 s or less, in some examples, 100 s or less, in some examples, 90 s or less, in some examples, 80 s or less, in some examples, 70 s or less, in some examples, 60 s or less, in some examples, 55 s or less, in some examples, 50 s or less, in some examples, 45 s or less, in some examples, 40 s or less, in some examples, 35 s or less, in some examples, 30 s or less, in some examples, 25 s or less, in some examples, 20 s or less, in some examples, 15 s or less, in some examples, 10 s or less, in some examples, 5 s or less before the current is measured. The sample suspected of containing the bacteria may be contacted with the electrode, the compound and/or the carrier medium 5 s or more, in some examples, 10 s or more, in some examples, 15 s or more, in some examples, 20 s or more, in some examples, 25 s or more, in some examples, 30 s or more, in some examples, 35 s or more, in some examples, 40 s or more, in some examples, 45 s or more, in some examples, 50 s or more, in some examples, 55 s or more, in some examples, 60 s or more, in some examples, 70 s or more, in some examples, 80 s or more, in some examples, 90 s or more, in some examples, 100 s or more, in some examples, 110 s or more, in some examples, about 120 s before the current is measured. The sample suspected of containing the bacteria may be contacted with the electrode, the compound and/or the carrier medium 0 s to 120 s before the current is measured. The sample suspected of containing the bacteria may be contacted with the electrode, the compound and/or the carrier medium 5 s to 110 s, in some examples, 10 s to 100 s, in some examples, 15 s to 90 s, in some examples, 20 s to 80 s, in some examples, 25 s to 70 s, in some examples, 30 s to 60 s, in some examples, 35 s to 55 s, in some examples, 40 s to 50 s, in some examples, 45 s to 50 s before the current is measured.

By measuring the current shortly after contacting the bacteria with the electrode, the compound and/or the carrier medium, bacteria cell death is minimized prior to measuring the current.

The Compound

The compound has two redox states: a reduced state and an oxidised state, wherein cytochrome c oxidase can convert the compound from its reduced state to its oxidised state. The compound may be any compound that can be oxidised by cytochrome c oxidase in a fully reversible electrochemical process. The compound may alternatively be any compound that can be oxidised by cytochrome c oxidase in an irreversible electrochemical process. The redox process may involve a one electron transfer. The compound may have a standard electrode potential (i.e. the reduction of the compound in its oxidised state to its reduced state) of between −1.5 V and 1.5 V, optionally between −1 V and 1V, optionally between −0.5 V and 0.5 V, optionally between −0.3 V and 0.3 V, optionally between −0.1 V and 0.1 V, optionally between 0 V and 0.1 V, optionally between 0.01 V and 0.03 V, optionally between 0.01 V and 0.015 V, optionally about 0.013 V, with all potentials vs. SCE. The compound may have a standard electrode potential (i.e. the reduction of the compound in its oxidised state to its reduced state) of between −1.5 V and 0 V, optionally between −1 V and 0 V, optionally between −0.5 V and 0 V optionally between −0.3 V and 0 V, optionally between −0.1 V and 0 V. The compound may have a standard electrode potential (i.e. the reduction of the compound in its oxidised state to its reduced state) of between 1.5 V and 0 V, optionally between 1 V and 0 V, optionally between 0.5 V and 0 V optionally between 0.3 V and 0 V, optionally between 0.1 V and 0 V.

The compound may have a standard electrode potential (i.e. the reduction of the compound in its oxidised state to its reduced state) of between 0 V and 0.1 V, optionally between 0.01 V and 0.03 V, optionally between 0.01 V and 0.015 V, optionally about 0.013 V, with all potentials vs. SCE.

The compound may be selected from a phenylene diamine, a polyphenol and a hydroquinone.

The compound may comprise a phenylene diamine, which may be a phenylene diamine radical cation or a combination of a phenylene diamine and a phenylene diamine radical cation. The phenylene diamine may be a para-phenylene diamine. The phenylene diamine may be a substituted phenylene diamine, for example, a nitrogen-substituted phenylene diamine. In an embodiment, a plurality of phenylene diamine having different structures are present.

The compound may be a phenylene diamine having one of the following structures:

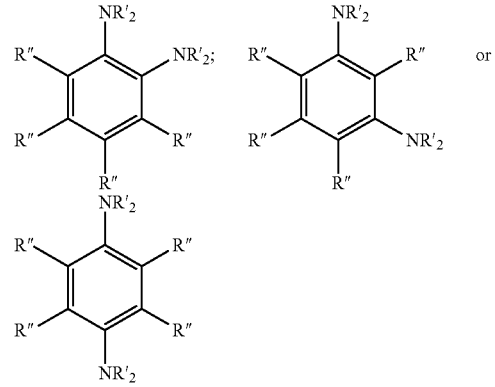

in which
each R' may be independently selected from hydrogen, alkyl, or alkenyl, wherein each alkyl may be a C1 to C6 alkyl and each alkenyl may be a C2 to C6 alkenyl; and
each R" may be independently selected from hydrogen, alkyl, or alkenyl, wherein each alkyl may be a C1 to C6 alkyl and each alkenyl may be a C2 to C6 alkenyl.

In some examples, each R" is hydrogen or methyl and each R' is independently selected from hydrogen, alkyl or alkenyl. In some examples, each R" is hydrogen and each R' is independently selected from hydrogen, alkyl or alkenyl. In some examples, each R" is hydrogen and each R' is independently selected from hydrogen, methyl or ethyl. In some examples, each R" is hydrogen and each R' is independently selected from hydrogen and methyl.

The phenylene diamine, optionally, the para-phenylene diamine may be selected from phenylene diamine, methylphenylene diamine, dimethylphenylene diamine, trimethylphenylene diamine, tetramethylphenylene diamine, ethylphenylene diamine, methylethylphenylene diamine, diethylphenylene diamine, dimethylethylphenylene diamine, methyldiethylphenylene diamine, triethylphenylene diamine, trimethylethylphenylene diamine, dimethyldiethylphenylene diamine, methyltriethylphenylene diamine and tetraethylphenylene diamine. The phenylene diamine, optionally the para-phenylene diamine, may be selected from N-methylphenylene diamine, N,N-dimethylphenylene diamine, N,N'-dimethylphenylene diamine, N,N,N'-trimethylphenylene diamine, N,N,N',N'-tetramethylphenylene diamine, N-ethylphenylene diamine, N-methyl-N-ethylphenylene diamine, N-methyl-N'-ethylphenylene diamine, N,N-diethylphenylene diamine, N,N'-diethylphenylene diamine, N,N-dimethyl-N'-ethylphenylene diamine, N,N'-dimethyl-N-ethylphenylene diamine, N,N,N'-triethylphenylene diamine, N-methyl-N',N'-diethylphenylene diamine, N-methyl-N,N'-diethylphenylene diamine, N,N,N'-tri-methyl-N'-ethylphenylene diamine, N,N-dimethyl-N',N'-diethylphenylene diamine, N,N'-dimethyl-N,N'-diethylphenylene diamine, N-methyl-N,N',N'-triethylphenylene diamine and N,N,N',N'-tetraethylphenylene diamine.

The phenylene diamine may be a tetramethylphenylene diamine, for example, a tetramethyl-para-phenylene diamine, for example, an N,N,N',N'-tetramethylphenylene diamine such as N,N,N',N'-tetramethyl-para-phenylene diamine. The phenylene diamine may be a dimethylphenylene diamine, for example, a dimethyl-para-phenylene diamine, for example, an N,N-dimethylphenylene diamine or an N,N'-dimethylphenylene diamine, such as an N,N- or N,N'-dimethyl-para-phenylene diamine.

The compound may comprise a tetramethylphenylene diamine radical cation, for example, an N,N,N',N'-tetramethyl-para-phenylene diamine radical cation. The phenylene diamine may be a phenylene diamine hydrochloride, a phenylene diamine dihydrochloride, a phenylene diamine tetrafluoroborate or a phenylene diamine oxalate. The phenylene diamine may be selected from N,N,N',N'-tetramethyl-para-phenylene diamine hydrochloride, N,N,N',N'-tetramethyl-para-phenylene diamine dihydrochloride, N,N,N',N'-tetramethyl-para-phenylene diamine tetrafluoroborate, N,N,N',N'-tetramethyl-para-phenylene diamine oxalate, N,N- or N,N'-dimethyl-para-phenylene diamine hydrochloride, N,N- or N,N'-dimethyl-para-phenylene diamine dihydrochloride, N,N- or N,N'-dimethyl-para-phenylene diamine tetrafluoroborate, and N,N- or N,N'-dimethyl-para-phenylene diamine oxalate.

The compound may be a mixture of N,N,N',N'-tetramethyl-para-phenylene diamine tetrafluoroborate and N,N,N',N'-tetramethyl-para-phenylene diamine. The compound may be a 3:1 mixture of N,N,N',N'-tetramethyl-para-phenylene diamine tetrafluoroborate and N,N,N',N'-tetramethyl-para-phenylene diamine.

The compound may be a polyphenol selected from quercetin and other flavonoids, such as catechin, catechin gallate, epicatechin and epicatechin gallate. Such flavoids are sometimes termed green tea catechins. Accordingly, the compound may be selected from a green tea catechin.

The compound may comprise, but is not limited to, N,N-dimethyl-para-phenylene diamine and the method may further comprise mixing the compound with naphthol, for example, alpha-naphthol, prior to contacting the compound with the electrode.

The compound may be in a carrier medium. The carrier medium may be a liquid carrier medium. The carrier medium may be the same as or miscible with the carrier medium in which the sample suspected of containing the bacteria is placed. The carrier medium may be an aqueous carrier medium.

The carrier medium may be a supporting electrolyte. The supporting electrolyte may be isotonic and non-toxic to bacteria.

The supporting electrolyte may comprise an aqueous carrier medium and a buffer. The buffer may be selected from a phosphate buffer, a boric acid buffer, a glycine buffer and buffers comprising salts of bicarbonate. The supporting electrolyte may be an aqueous supporting electrolyte having a pH of from 5 to 9, optionally, from 6 to 8, optionally from 6.5 to 7.5.

The supporting electrolyte may be a buffered saline, which may be selected from phosphate buffered saline (PBS) or tris(hydroxymethyl)aminomethane (Tris) buffered saline.

Phosphate buffered saline may comprise a combination of one or more phosphate salts with one or more chloride salts. The phosphate salts may be selected from sodium phosphate dibasic, sodium phosphate monobasic, potassium phosphate dibasic, potassium phosphate monobasic or combinations thereof. The chloride salts may be selected from sodium chloride, potassium chloride, calcium chloride, magnesium chloride or combinations thereof. Phosphate buffered saline may comprise sodium phosphate dibasic and sodium chloride. Phosphate buffered saline may comprise sodium phosphate dibasic, potassium phosphate dibasic, sodium chloride and potassium chloride.

Tris buffered saline may comprise tris(hydroxymethyl)aminomethane chloride and sodium chloride.

The electrode may comprise any suitably conducting material, for example, a metal, an alloy of metals, and/or carbon. The electrode may comprise a transition metal for example, a transition metal selected from any of groups 9 to 11 of the Periodic Table. The electrode may comprise a metal selected from, but not limited to, rhenium, iridium, palladium, platinum, copper, indium, rubidium, silver and gold. The electrode may be a gold macroelectrode. If the electrode comprises carbon, the carbon may be selected from edge plane pyrolytic graphite, basal plane pyrolytic graphite, a glassy carbon, boron doped diamond, highly ordered pyrolytic graphite, carbon powder and carbon nanotubes.

Method of Determining the Presence of Bacteria Expressing Cytochrome c Oxidase

The compound having two redox states may be combined with a carrier medium.

The sample suspected of containing the bacteria may be combined with a carrier medium and then combined with the carrier medium containing the compound. Alternatively, the sample suspected of containing the bacteria may be added directly to the carrier medium containing the compound. An electrode is then added to the carrier medium containing the compound in the presence of the sample. Alternatively, the sample suspected of containing the bacteria is immobilised on the surface of an electrode and then the electrode is added to the carrier medium containing the compound.

If the compound is provided as a mixture of the compound in the oxidised state and the compound in the reduced state, either (i) involves, before applying the reductive potential, an oxidative potential is applied to covert at least some of, optionally all of, the compound in its reduced state to the compound in its oxidised state or (ii) involves, before applying the oxidative potential, a reductive potential is applied to convert at least some of, optionally all of, the compound in its oxidised state to the compound in its reduced state. The application of this (i) oxidative potential or (ii) reductive potential may convert all of the compound within the diffusion layer surrounding the electrode into the (i) oxidised state or (ii) reduced state.

When the compound is in its oxidised state in the presence of the sample suspected of containing the bacteria, a reductive potential is applied. The reductive potential converts the compound into the substrate for cytochrome c oxidase to oxidise, that is, the reduced form of the compound. In the presence of a bacteria expressing cytochrome c oxidase, the concentration of oxidised compound for the reductive potential to reduce is increased relative to the concentration in the absence of the bacteria, causing a higher magnitude of current to be produced and measured in the electrochemical circuit.

When the compound is in its reduced state in the presence of the sample suspected of containing the bacteria, an oxidative potential is applied. The oxidative potential converts the compound into the oxidised form of the compound, producing a current in the electrochemical system. In the presence of a bacteria expressing cytochrome c oxidase, the bacteria also convert the compound from the reduced form to the oxidised form, reducing the concentration of the compound in the vicinity of the electrode and thus reducing the magnitude of the current produced and measured in the electrochemical circuit in comparison to in the absence of the bacteria expressing cytochrome c oxidase.

If it is determined that the sample contains the bacteria, the difference between the magnitude of the current produced in the presence of the sample containing the bacteria and the magnitude of the current produced in the absence of the sample containing the bacteria can be used to determine the activity of cytochrome c oxidase in the bacteria by determining the turnover number per single bacteria. The turnover number per single bacteria ($T_{sb}$) can be determined by using the following equation:

$$T_{sb} = \frac{\Delta I}{fNeC}$$

in which $\Delta I$ is the difference between the magnitude of current produced in the presence of the sample containing the bacteria and the magnitude of current produced in the absence of the sample containing the bacteria;

f is the viability factor for the bacteria;

N is the number of bacteria in the sample;

e is the charge of an electron ($1.6 \times 10^{-19}$ As); and

C is the concentration of the compound.

Once the turnover number per single bacteria has been determined by using this equation, the bacteria can be identified by comparing the turnover number per single bacteria with a database of turnover numbers per single bacteria for a variety of different bacteria.

Alternatively, if it is determined that the sample contains the bacteria and the bacteria is identified, the method may further comprise determining the number of bacteria present by comparing the normalised current difference to a calibration curve in which the normalized current difference for the bacteria has been plotted against the number of bacteria in several calibration samples. The normalised current difference may be the difference between the magnitude of the current produced in the presence of the sample containing the bacteria and the magnitude of the current produced in the absence of the sample containing the bacteria divided the magnitude of the current produced in the absence of the sample containing the bacteria. In some examples, a linear calibration curve is obtained for samples containing up to a certain number of bacteria, for example, $1 \times 10^7$ bacteria, before electrode blockage is observed for higher concentrations of bacteria.

Alternatively, if the identity of the bacteria found to be present in the sample is determined, the number of bacteria in the sample can be determined by using the following equation:

$$N = \frac{\Delta I}{T_{sb}feC}$$

in which $\Delta I$ is the difference between the magnitude of current produced in the presence of the sample containing the bacteria and the magnitude of current produced in the absence of the sample containing the bacteria;

$T_{sb}$ is the turnover number per single bacteria;

f is the viability factor for the bacteria;

e is the charge of an electron ($1.6 \times 10^{-19}$ As); and

C is the concentration of the compound.

Electrochemical Sensor

In a second aspect, there is provided an electrochemical sensor for determining the presence of bacteria expressing cytochrome c oxidase ("the bacteria") in a sample suspected of containing the bacteria. The electrochemical sensor comprises:

an electrode; and a compound that has two redox states: a reduced state and an oxidised state, wherein cytochrome c oxidase can convert the compound from its reduced state to its oxidised state; and the sensor is adapted to:

contact the electrode with a sample suspected of containing the bacteria and either with (i) the compound in its oxidised state, then apply a reductive potential and measure the current at the electrode; or (ii) the compound in its reduced state, then apply an oxidative potential and measure the current at the electrode; and compare the magnitude of the current produced by the reductive potential or oxidative potential in the presence of the sample suspected of containing the bacteria with the magnitude of the current produced under the same conditions, but in the absence of the sample suspected of containing the bacteria, wherein a difference between the magnitude of current produced in the presence of the sample suspected of containing the bacteria and the magnitude of current produced in the absence of the sample suspected of containing the bacteria indicates the presence of the bacteria.

In an embodiment, the bacteria may be immobilized by attachment to the surface of the electrode by a species selective for the bacteria, for example, a species selected from an antibody, an antibody fragment, an aptamer and a bacteriophage (e.g. a T4 bacteriophage). The species selective for the bacteria may be termed a probe molecule. The electrode may have, immobilised on a surface thereof, a species selective for the bacteria, for example, a species selected from an antibody, an antibody fragment, an aptamer and a bacteriophage (e.g. a T4 bacteriophage). The antibody may be selected from a monoclonal antibody or a polyclonal antibody. These may allow the limit of detection to be lowered compared to non-selective electrodes, and, because of the selectivity, allow it to be determined if certain bacteria are present in a sample (with only those for which the electrode is selective adhering to the electrode after exposure to the sample).

The electrode surface may have probe molecules thereon and, as a whole, may be selective for the bacteria. If the electrode surface having the probe molecules thereon is selective for the bacteria, this indicates that substantially only or only the bacteria will bind to the surface (binding to the probe molecules), and other species (e.g. present in the carrier medium with the bacteria) will not bind, or not bind to any significant degree, to other parts of the electrode surface or other species thereon. For example, the electrode surface may comprise a self-assembling monolayer of linker molecules, some of which are bound to probe moieties, e.g. antibodies, that selectively bind to the bacteria. When in a liquid carrier medium, e.g. a sample, the electrode surface preferably only binds to the bacteria, not to other species present in the liquid carrier medium. Such selective electrode surfaces may be termed highly selective electrode surfaces.

In an embodiment, the probe molecule is of the formula A-L-B, where A is a moiety that binds to the surface of the electrode, L is a linker moiety and B is a moiety which binds to the bacteria.

'A' may be selected from an appropriate binding group, depending on the nature of the material of the electrode. A may be selected from, but is not limited to, biotin, hydrazine, alkynyl, alkylazide, amino, hydroxyl, carboxy, thio, aldehyde, phosphoinothioester, maleimidyl, succinyl, succinimidyl, isocyanate, ester, strepavidin, avidin, neuavidin, and biotin binding proteins. If the electrode comprises a noble material, e.g. gold, silver or platinum, A is preferably thio, which may be selected from —SH and —S—. If the electrode comprises a metal that has a layer of oxide on its surface, e.g. copper, A may be a carboxy group.

L may be any species that covalently links A with B. L is preferably a species that allows formation of a self-assembling monolayer. L may comprise an alkylene moiety comprising at least 2 carbons, the alkylene moiety being directly attached to A; optionally the alkylene moiety is a straight-chain alkylene moiety. L may comprise an alkylene moiety comprising at least 5 carbons, optionally from 5 to 30 carbons, optionally from 5 to 20 carbons, optionally from 5 to 15 carbon atoms, optionally from 7 to 15 carbon atoms, optionally from 9 to 11 carbon atoms and the alkylene moiety is optionally a straight-chain alkylene moiety, and the alkylene moiety is directly attached to A.

In an embodiment, L is of the formula —(CH$_2$)$_n$—(—O—CH$_2$—CH$_2$—)$_m$-D-, wherein n is from 1 to 30 and m is from 0 to 10, optionally n is from 1 to 30, optionally 5 to 30, optionally 5 to 15, and m is 0 and D is a group that binds to B. D may be selected from a single bond, —(C=O)—, —OCH$_2$—(C=O)—, —(C=O)—NH—, —(C=O)—O—OCH$_2$—(C=O)—NH—, —OCH$_2$—(C=O)—OH—, —O—, —NH—. n may be from 10 to 20. m may be 1 to 5, optionally 2 to 4, optionally 3. Optionally, m is 0 and n is from 1 to 30, optionally from 5 to 15, optionally from 7 to 15, optionally from 9 to 13, optionally 10, 11 or 12. Optionally, if D is any one of the species (C=O)—NH—, —(C=O)—O—, —OCH$_2$—(C=O)—NH—, —OCH$_2$—(C=O)—O—, —O— and —NH—, then —NH— or —O— in these species may be derived from a probe molecule, e.g. antibody, prior to being bound to the linker species L.

B may be selected from a binding species as described above, for example selected from an antibody, an antibody fragment, an aptamer, an oligosaccharide, a peptide, a protein. Such species that bind selectively to bacteria, are available commercially.

In an embodiment, A-L- is a species of the formula thio-(CH$_2$)$_n$—(—O—CH$_2$—CH$_2$—)$_m$-D-, wherein n is from 1 to 30 and m is from 0 to 10 and D is a group that binds to B; optionally n, m and D may be as defined above, and thio is selected from —S— and HS—.

In an embodiment, A-L- is a species of the formula thio-(CH$_2$)$_n$—(—O—CH$_2$—CH$_2$—)$_m$-D-, wherein n is from 1 to 30, optionally from 5 to 15, optionally from 7 to 15, optionally from 9 to 13, optionally 10, 11 or 12 and m is from 0 to 10 and D is —NHCOBiotin-(neutr)avidin-, and thio is selected from —S— and HS—, and B is a biotinylated binding species that selectively binds to the bacteria (with the biotin group of the biotinylated binding species being bound to the (neutr)avidin of A-L-), for example selected from a biotinylated antibody, a biotinylated antibody fragment, a biotinylated aptamer, a biotinylated oligosaccharide, a biotinylated peptide and a biotinylated protein. (neutr)avidin- indicates a species selected from neutravidin and avidin.

In an embodiment, A-L- is a species of the formula thio-(CH$_2$)$_n$—(—O—CH$_2$—CH$_2$—)$_m$-D-, wherein n is from 1 to 30, optionally from 5 to 15, optionally from 7 to 15, optionally from 9 to 13, optionally 10, 11 or 12 and m is from 0 and D is —NHCOBiotin-(neutr)avidin-, and thio is selected from —S— and HS—, and B is a biotinylated binding species that selectively binds to the bacteria (with the biotin group of the biotinylated binding species being bound to the (neutr)avidin of A-L-), for example selected from a biotinylated antibody, a biotinylated antibody fragment, a biotinylated aptamer, a biotinylated oligosaccharide, a biotinylated peptide and a biotinylated protein. (neutr)avidin- indicates a species selected from neutravidin and avidin.

B is preferably capable of binding selectively to the bacteria. B preferably comprises or is a binding species selected from an antibody, an antibody fragment, an aptamer, an oligosaccharide, a peptide, and a protein. B preferably comprises or is a binding species selected from one or more of an antibody, an antibody fragment, a nucleic acid and a peptide. Preferably, the probe moieties bind selectively to the bacteria If B comprises or is an antibody or an antibody fragment, the antibody or the antibody fragment may be selected from one or more of the classes IgA, IgD, IgE, IgG and IgM. The antibody or antibody fragment preferably binds selectively to C-reactive protein.

If B comprises or is an aptamer, the aptamer may be selected from a peptide aptamer, a DNA aptamer and a RNA aptamer.

In an embodiment, an electrode as described herein, e.g. having probe molecules thereon, may be produced by providing the electrode having the planar surface, then forming a self-assembling monolayer of linker species on the planar surface, and attaching probe moieties, e.g. antibodies, that bind to the bacteria to at least some of the linker species. In an embodiment, the linker species forming the self-assembling monolayer are of the formula A-L as defined above.

Optionally, spacer molecules may also be present on the surface of the electrode. Optionally the surface of the electrode may have thereon the probe molecules and spacer molecules, optionally a self-assembling monolayer comprising the probe molecules and the spacer molecules. The spacer molecules do not bind to the bacteria, and may be any species capable of forming a self-assembling monolayer on the surface, while not impeding the binding of the probe molecules to the bacteria, e.g. the spacer moleculers are preferably not longer, and are ideally shorter in length, than the probe molecules. The spacer molecules may be of the formula -A-L-H (H being hydrogen), with A and L being as defined above, but they may not be the same as those of the probe molecules. In an embodiment, L is of the formula —$(CH_2)_n$—$(—O—CH_2—CH_2—)_m$—H, wherein n is from 1 to 30 and m is from 0 to 10, optionally n is from 1 to 30, optionally 5 to 30, optionally 5 to 15, optionally 5 to 15, optionally 6, 7, 8 or 9 and m is from 0. The spacer molecules may be present in the same or a greater amount, in moles, on the surface of the electrode than the probe molecules. The molar ratio of probe molecules to spacer molecules may be from 1:1 to 1:10, optionally 1:2 to 1:6, optionally about 1:4.

Optionally, any unspecific reactive sites in the species on the surface of electrode (e.g. from the linker, the spacer molecules and/or the probe molecules), e.g. thiols, may be blocked with a suitable species, e.g. a suitable protein such as bovine serum albumin (BSA).

The electrochemical sensor may further comprise a counter electrode. The electrochemical sensor may further comprise a counter electrode and a reference electrode. For the avoidance of doubt, the electrode having a sample suspected of containing the bacteria may be termed a working electrode herein. A potential may be applied between a working electrode and a counter electrode and the resulting current measured, for example, using a potentiostat.

The shape and configuration of the electrodes is not particularly restricted. The electrodes may be in the form of points, lines, rings or flat planer surfaces. In an embodiment, the working electrode and the counter electrode are disposed opposite one another within a housing. In an embodiment, the working electrode and reference electrode are disposed on the same face of a housing or a substrate. In an embodiment, one or more working electrodes may be disposed on a substrate, and, in an embodiment, a plurality of recesses, which may be in the form of channels, may be disposed on the substrate, with a working electrode in each of the recesses. This may provide for testing a plurality of samples with the same substrate, for example a recess for testing (i) a sample in which the nature and/or content of the bacteria is unknown, and one or both of (ii) a sample is which the nature and/or content of the bacteria is known (i.e. a positive control) and/or (iii) a sample lacking bacteria (i.e. a negative control). In an embodiment, the substrate, e.g. with the plurality of recesses and/or working electrodes may be in portable form, e.g. in a form that may be held in a human hand, e.g. in the form of a sheet, with dimensions across the sheet (in any direction) of, for example, 20 cm or less, optionally 15 cm or less, optionally 12 cm or less, optionally 10 cm or less, optionally 9 cm or less, optionally 10 cm or less. The substrate may, for example, be of a similar size and shape as a credit card (e.g. about 5 to 6 cm in one direction across the substrate and from 8 to 10 cm in a perpendicular direction across the substrate). The substrate having a plurality of working electrodes thereon may also have one or more counter electrodes thereon, e.g. a counter electrode corresponding to each of the working electrodes.

The working electrode and counter electrode may have any appropriate size, for example, a maximum distance across their face of from 1 nm to 10 cm, optionally from 10 nm to 5 cm, optionally, from 100 nm to 1 cm, optionally, from 500 nm to 5 mm, optionally, 1 micron to 1000 microns, optionally from 1 micron to 500 microns, optionally from 1 micron to 50 microns. The gap between the working electrode and the counter electrode may be from 20 nm to 10 cm, optionally, from 200 nm to 5 cm, optionally, from 2 microns to 1 cm, optionally from 20 microns to 1000 microns, optionally from 50 microns to 500 microns.

The working electrode and counter electrode are optionally of equal size. Alternatively, the surface area of the counter electrode is greater than that of the working electrode.

The counter electrode and, if present, the reference electrode may each comprise any suitable electrically conductive material. The electrically conductive material may be the same or different from the electrically conducting material of the working electrode and may comprise materials selected from the same list of materials.

The electrochemical sensor may contain an appropriate computer program for controlling the electrochemical sensor such that the method as described herein is carried out. The computer program may be on suitable hardware, firmware or other storage media that may form part of the electrochemical sensor.

EXAMPLES

Example 1

Materials

All chemicals were purchased from Sigma-Aldrich, if not indicated otherwise. Phosphate buffered saline (PBS) solution consists of 8 g sodium chloride (99%), 0.2 g potassium chloride (99%), 1.44 g sodium phosphate dibasic (99%), 0.24 g potassium phosphate dibasic (99%) and was made up to 1 L using nanopure water with a resistivity of not less than 18.2 MO cm at 25° C. (Millipore water purification system).

Synthesis of TMPD-$BF_4$

The compound N,N,N',N'-tetramethyl-para-phenylene diamine (TMPD) is rapidly oxidized by atmospheric oxygen, therefore the radical cation salt N,N,N',N'-tetramethyl-para-phenylene diamine tetrafluoroborate (TMPD-$BF_4$) was synthesized, to assure solution stability and higher accuracy during bioelectrochemical measurements.

The radical cation salt TMPD-$BF_4$ was prepared by following the method of Yamauchi et al.[24] In short, TMPD (99%) was dissolved in 18 ml nanopure $H_2O$ and 24 ml methanol, containing 9 g sodium tetrafluoroborate (Alfa Aesar, UK, 97%). Aqueous bromine solution (32 ml, 0.252 mol kg$^{-1}$) was added dropwise to the cooled TMPD solution (−10° C.). The resulting crystals were washed repeatedly with ice-cold methanol, followed by dry ether. Crystals appeared brownish purple, in accordance with the literature [24], and a melting point of 125-127° C. was determined.

Analysis and Identification of TMPD-$BF_4$

Figure 2:
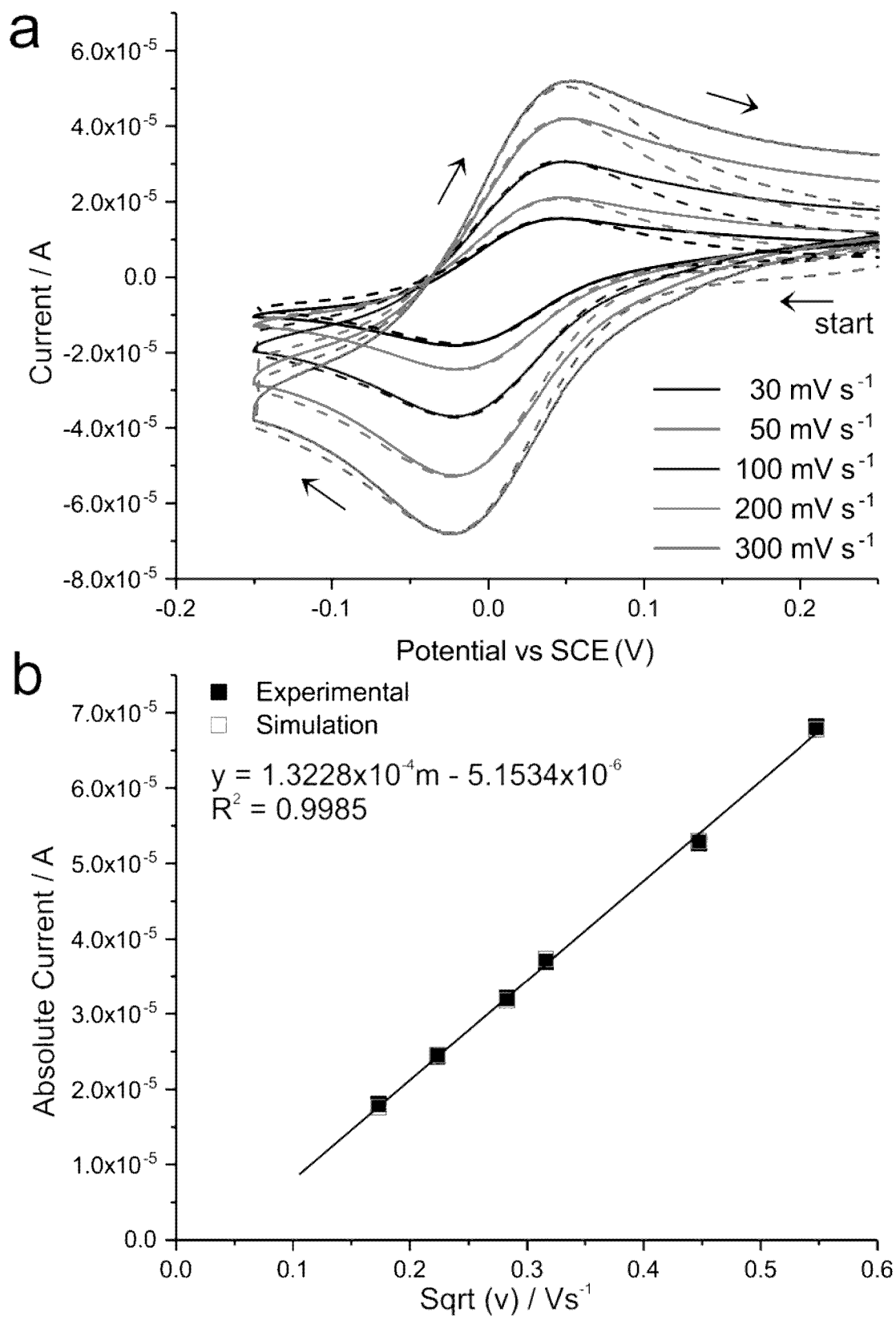

A product composition of ~75% TMPD-$BF_4$ and 25% TMPD in solution was determined (see FIG. 1) electrochemically (by cyclic voltammetry and using the equation $$C = \frac{I_{ss}}{4FDa}$$

in which C is the concentration, $I_{ss}$ represents the steady state current, F is the Faraday constant, D is the diffusion coefficient and a is the radius of the electroactive surface of the microelectrode), and its electrochemical behaviour was analysed using cyclic voltammetry. FIG. 2a shows cyclic voltammograms recorded by using a 3 mm gold macroelectrode in 2.1 mM TMPD-BF$_4$ in PBS buffer solution (0.17 M), which functions as a supporting electrolyte. Various scan rates, ranging from 30 to 300 mV s$^{-1}$, were applied. As the singly oxidized form of TMPD, the TMPD$^{+\bullet}$ radical cation can be reduced to TMPD and oxidized to TMPD$^{2+}$:

$$\text{TMPD}^{+\bullet} + e^- \rightleftharpoons \text{TMPD} \quad (1)$$

$$\text{TMPD}^{2+} + e^- \rightleftharpoons \text{TMPD}^{+\bullet} \quad (2)$$

in which only the first redox reaction is fully reversible, [25] and will be the focus of this method. Using the commercial simulation software DigiSim® (Basi), theoretical curves were fitted to the experimental data.[26-30] FIG. 2b shows the linear behaviour of the TMPD-BF$_4$ peak current as a function of the square root of scan rate, which can be used for the extraction of a diffusion coefficient by using the Randles-Ševćik equation. A diffusion coefficient $D_{TMPD-BF_4}$ of $1.0 \times 10^{-5}$ cm$^2$ s$^{-1}$ was determined for a solution temperature of 37° C. and fixed in the DigiSim® program. Detailed information about the calculation of $D_{TMPD-BF_4}$ can be found below. Following the approach in the literature,[31] the redox reaction (1) was simulated to determine the Butler-Volmer kinetic parameters of TMPD$^{+\bullet}$ reduction at the macroelectrode and a fitting of the concentration-independent heterogeneous standard electrochemical rate constant (k$_s$), as well as the standard electrode potential E$_0$, was conducted. To account for minor solution changes related to the oxidation of TMPD by oxygen, the initial concentration ratio of TMPD to TMPD$^{+\bullet}$ was slightly adjusted for each scan without changing the overall shape or position of the simulated curves. This allowed an offset correction for the presented curves and a capacitive contribution of between 10 to 30 μF was attributed. From the simulations, the standard electrochemical rate constant k$_s$ was determined to be equal to or greater than 0.025 cm s$^{-1}$, and a standard electrode potential E$_0$ of 0.013 (±0.001) V vs. SCE was determined. The resulting theoretical voltammograms (FIG. 2a, dotted lines) are in good agreement with the experimental measurements (full lines). The electrochemical characterization of TMPD-BF$_4$, its solubility and stability make it a suitable redox mediator for the analysis of pathogenic and non-pathogenic bacterial oxidases.

Bacteria Culture

*Escherichia coli*

Bacteria were cultured in 2×TY liquid microbial growth medium (broth), containing 16 g L$^{-1}$ tryptone, 10 g L$^{-1}$ yeast extract and 5.0 g NaCl. Growth medium was inoculated with bacteria from frozen stocks and incubated in glass culture flasks for 18 h at 37° C. in an incubator shaker (Model G25, New Brunswick Scientific, USA). An *E. coli* suspension of 50 μL was transferred into a new culture flask, containing fresh growth medium. Following incubation for 3 to 4 h at 37° C., the number of bacteria in solution was determined by optical density (OD) at a wavelength of 600 nm (OD$_{600}$ of 1.0=8×10$^8$ cells mL$^{-1}$).[36] When an OD between 0.4 and 1.8 was reached, bacteria were harvested by centrifugation (Centrifuge 5702, Eppendorf, UK) for 15 min at 3000 rcf and re-suspended in pre-warmed (37° C.) PBS.

*Bacillus subtilis* (Strain PY79)

Low salt growth medium (broth; BD Bacto, UK), containing 10 g L$^{-1}$ tryptone, 5.0 g yeast extract and 5.0 g L$^{-1}$ sodium chloride, was inoculated with cultures from frozen stocks and incubated at 30° C. for 36 h in an incubator shaker (Multitron Pro, Infors HT, UK). An OD$_{600}$ was determined to calculate number of bacteria in solution (OD$_{600}$ of 1.0=5×10$^8$ cells mL$^{-1}$).[37,38] Bacteria were harvested by centrifugation for 10 min at 300 rcf and re-suspended in pre-warmed (30° C.) PBS. Cultures grown on agar, containing 10 g L$^{-1}$ tryptone, 5.0 g L$^{-1}$ yeast extract, 5.0 g L$^{-1}$ sodium chloride and 20 g L$^{-1}$ agar, were inoculated onto LB36 plates and grown at 30° C. for 36 h in a static incubator (HeraTherm, Thermo Fisher, UK).

Colorimetric Oxidase Test

Figure 4:
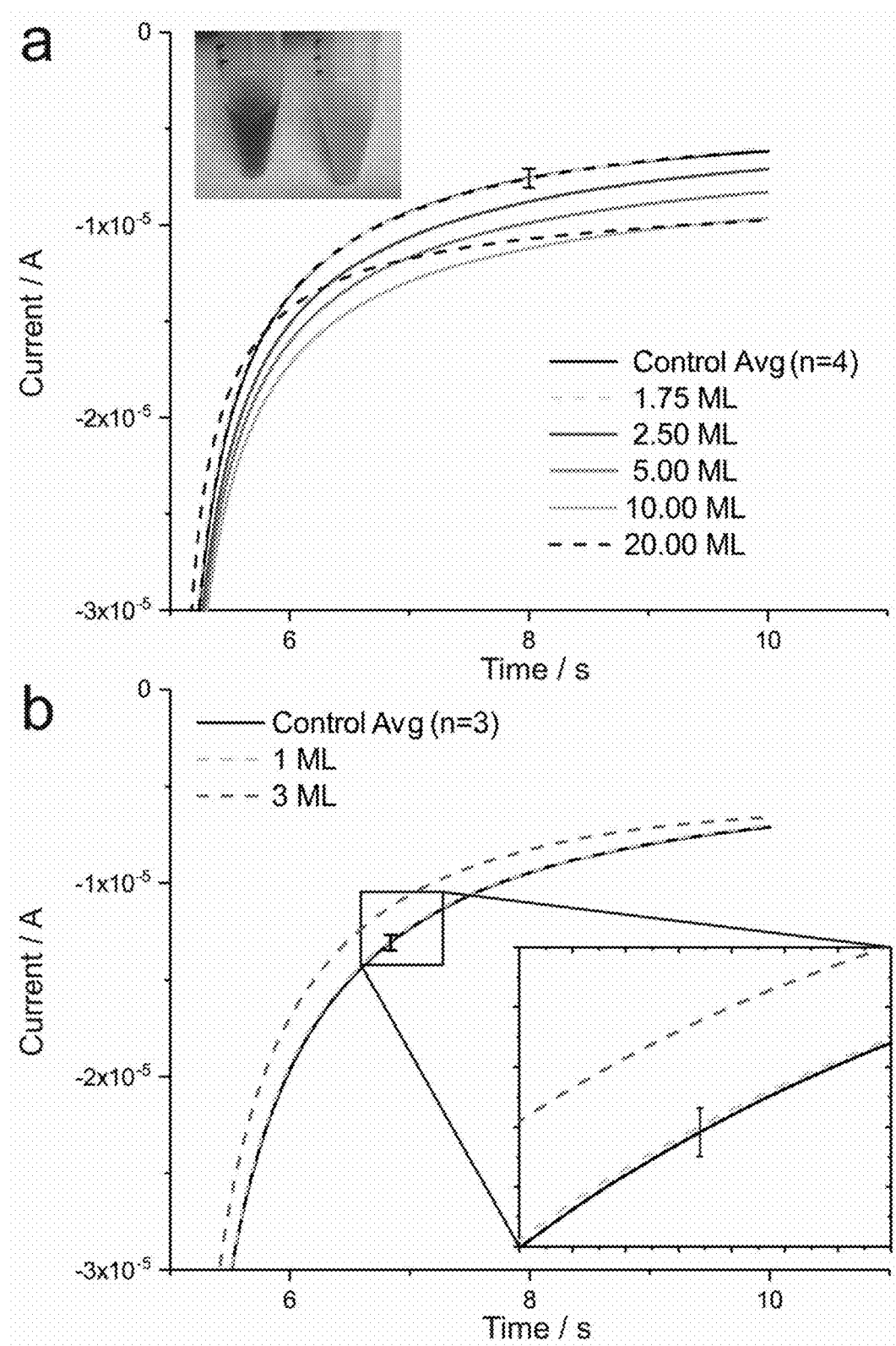

200 μL of a 1% (wt.) N,N,N',N'-Tetramethyl-p-phenylene diamine dihydrochloride (TMPD-2HCl) solution was added to 1 mL of cell suspension (1×10$^7$ cells μL$^{-1}$). Images were taken within 30 s of solution mixture. The chemical oxidation of TMPD to TMPD$^{+\bullet}$ can be observed in a test tube as a colour change, as shown in FIG. 4a (inset). This is known as the "oxidase test" in enzymology and microbiology. A colour change from colourless to deep blue indicates the presence of cytochrome c oxidase activity.

The colorimetric oxidase test on a sample of *B. subtilis* shows an immediate colour change to a deep blue colour. In contrast, the colorimetric oxidase test performed on a sample of *E. coli* shows no colour change, with the sample remaining colourless.

Electrochemical Measurements

Electrochemical measurements were carried out using a modular potentiostat (PGSTAT302N, Autolab, UK). All experiments involving bacteria cultures were conducted at 37° C. inside a Faraday cage. An in-house fabricated gold microelectrode with a diameter of 6.9 μm was employed to determine the concentration of TMPD-BF$_4$ in solution by cyclic voltammetry (see above for the method of determining the concentration). Working electrodes were polished prior to experiments using a water-alumina mix (1.0, 0.3 and 0.05 μm, 30 seconds for each grade) on microcloth polishing pads (Buehler, USA).[39] In all experiments, a saturated calomel electrode (SCE) and a platinum mesh were employed as reference and counter electrodes, respectively.

Recognition of Cytochrome c Oxidase by Bioelectrochemical Measurement

Figure 3:
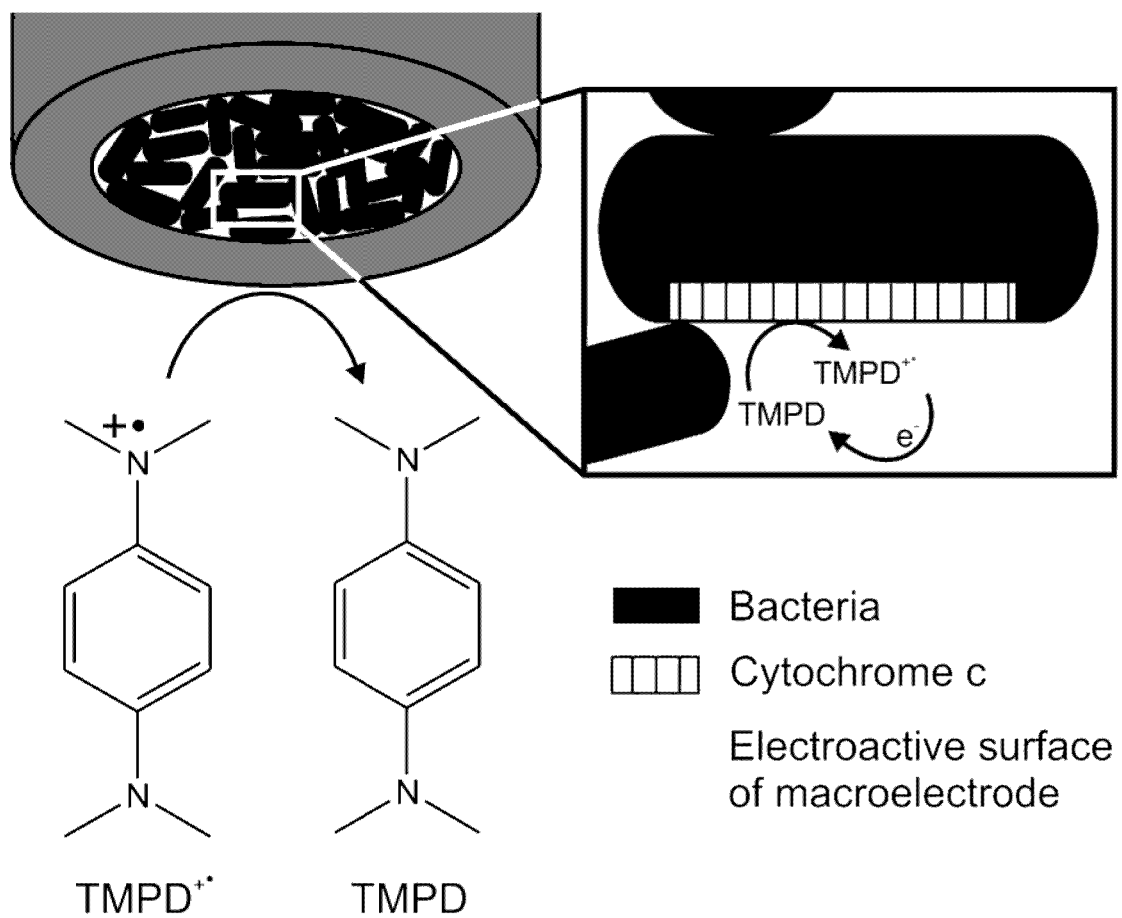

For the localized electrochemical recognition of cytochrome c oxidases in bacteria, target cultures were immobilized onto a gold macroelectrode by drop-casting and immersed into a solution of PBS, containing 1.7 mM TMPD$^{+\bullet}$ (FIG. 3). The radical cation can be reduced electrochemically at the electrode to TMPD, providing the substrate for the target bacteria to oxidise and convert TMPD back to TMPD$^{+\bullet}$. The chemical oxidation of TMPD to TMPD$^{+\bullet}$ can then be observed electrochemically.

A 3 mm (diameter) gold macroelectrode (Alvatek Ltd, UK) was used as the working electrode for all bioelectrochemical measurements. After polishing, sonication of the macroelectrode was applied for 2 minutes to assure removal of alumina powder from the electrode surface. Bacteria were immobilized onto the electrode by drop casting. For this purpose, the macroelectrode was placed in an electrode holder inside a 50 mL falcon tube, keeping it in an upright position. Bacteria suspension was diluted so that all depositions consisted of 3 μL bacteria suspension representing monolayer concentrations of 0.5 to 30. The falcon tube was closed and the bacteria suspension dried under N$_2$ flow. Evaporation was monitored by eye and N$_2$ flow was stopped the moment all liquid was evaporated. The electrode was removed from the holder and was placed in the electrochemical set up. The electrochemical cell remained thermostated to 37° C. throughout the experiments.

Chronoamperometry was carried out immediately after drop-casting of bacteria to minimize cell death at the electrode. In the case of *E. coli* organisms, a delay time of 45 s was applied after the electrode was brought in contact with the solution, holding the electrode at open circuit potential.

An oxidative potential of 250 mV was applied for 5 s, followed by a potential step to a reductive regime of −150 mV, which was held for 5 s also. All potentials are indicated vs. a saturated calomel reference electrode (SCE).

B. subtilis bacteria (cultured on agar) at different concentrations, ranging from $3.5 \times 10^6$ cells to $4 \times 10^7$ cells (1.75 to 20 monolayers (ML)), were drop-cast onto the working electrode. By applying an oxidative potential far exceeding the standard potential of TMPD during chronoamperometry, any anions remaining in the diffusion layer of the electrode are converted to $TMPD^{+\bullet}$. An immediately following step potential to the reductive regime, generates TMPD as an artificial electron donor for B. subtilis' cytochrome c oxidases. FIG. 4a shows an increase in the magnitude of the electrochemical current in the presence of B. subtilis bacteria at the electrode, compared to the control that represents an unmodified electrode surface. A level of detection (LOD) of $5 \times 10^6$ bacteria at the electrode was determined, corresponding to a surface concentration of about 2.5 monolayers (ML), whereas electrode blockage was observed at a concentration of 20 ML. When cultured in broth instead of agar plates, B. subtilis results in a negative oxidase test (FIG. 4a, inset, test tube right) and can be employed as a negative control, as shown in FIG. 4b. Here, a concentration of 1 ML does not result in a measurable current increase and electrode blockage is already observed at a surface concentration of 3 ML. Error bars in all figures represent three times the standard deviation.

Figure 5:
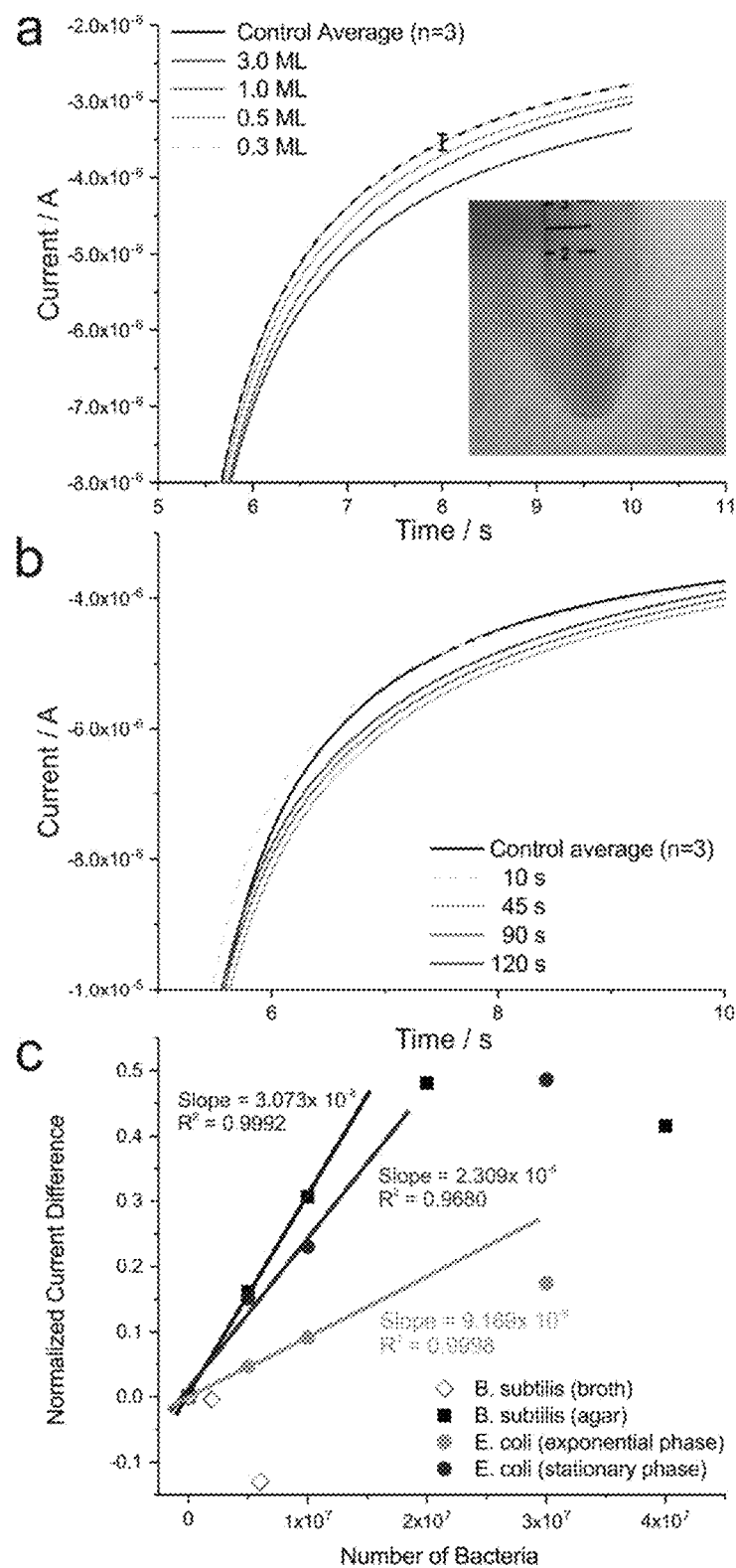

E. coli bacteria, cultured under aerobic conditions, were then investigated. In cell culture, standard oxidase tests performed under these conditions result in a negative outcome, missing the characteristic blue colour indication of $TMPD^{+\bullet}$ (FIG. 5a inset). Although E. coli bacteria do possess a ccm gene cluster in the aeg-46.5 operon region, which becomes important for the functional pathway involved in cytochrome c maturation [32], amounts of cytochrome c synthesised under aerobic bacteria growth cannot be detected by techniques in molecular biology, such as SDS-PAGE.[33] However, the genomic information of E. coli strongly suggests that cytochrome c maturation in this organism follows a pathway similar to the one that has been shown for other bacteria.[32] Furthermore, gradual gene activity levels as well as protein expression up and down regulation under conditions such as oxygen deprivation have been reported in the literature,[34] in contrast to straight forward on or off switch mechanisms. In fact, cytochrome c-heme lyase activity was found to be present in aerobic E. coli,[35] which gives reason to suspect a minimal expression of cytochrome c in E. coli even in the presence of oxygen. Interestingly, as it can be seen in FIG. 5a, a current increase in the presence of E. coli at the macroelectrode was observed despite a negative classical colorimetric oxidase test, demonstrating how electrochemical techniques have the potential to outperform other methods in molecular biology. Furthermore, FIG. 5b illustrates the dependency of the electrochemical current signal on an experimental delay time. After immobilization of E. coli bacteria, the electrode was placed in solution and kept for various delay times before a potential step was applied. At a delay time of 45 s, a maximum current response was achieved (FIG. 5b, red line), indicating that bacteria present require time to generate sufficient amounts of $TMPD^{+\bullet}$ to be recognized at the electrode. If a delay time of 90 s or greater applied, the concentration differences are thought to equilibrate and the current response decreases. The enhanced electrochemical signal in the presence of E. coli can also be recorded during cyclic voltammetry. However, due to the small current range detected, scan rates as low as 2 mV s$^{-1}$ need to be applied in order to visualize the oxidation process of TMPD by the bacteria. At these slow scan rates, a contribution to the current signals by convective effects has to be assumed. Consequently, chronoamperometry measurements were chosen for quantitative analyses.

Figure 6:
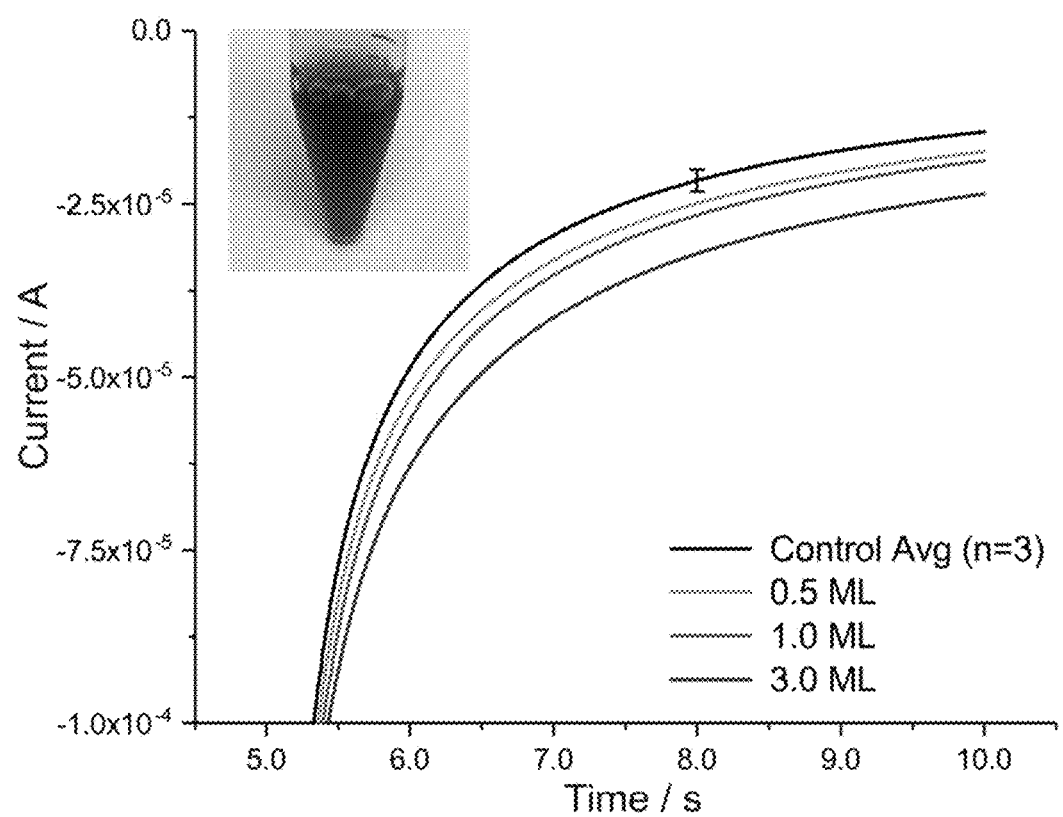

To promote an increased cytochrome c maturation in E. coli, bacteria were cultured to the stationary phase, which results in a positive colorimetric oxidase test in E. coli (FIG. 6, inset), probably due to the competition for oxygen in solution. As expected, the increased cytochrome c oxidase activity under these growth conditions can be seen electrochemically and is presented in FIG. 6.

Figure 7:
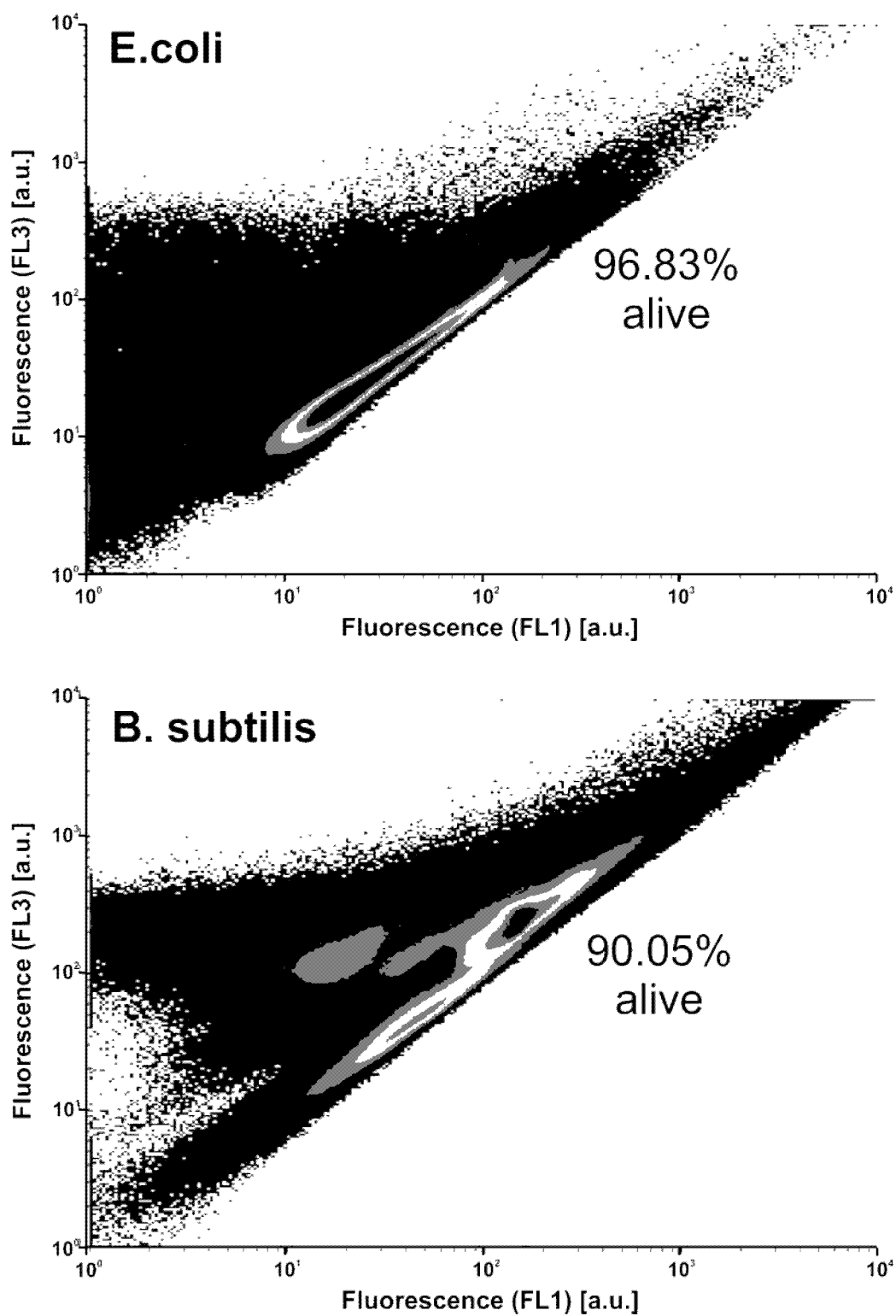
Figure 8:
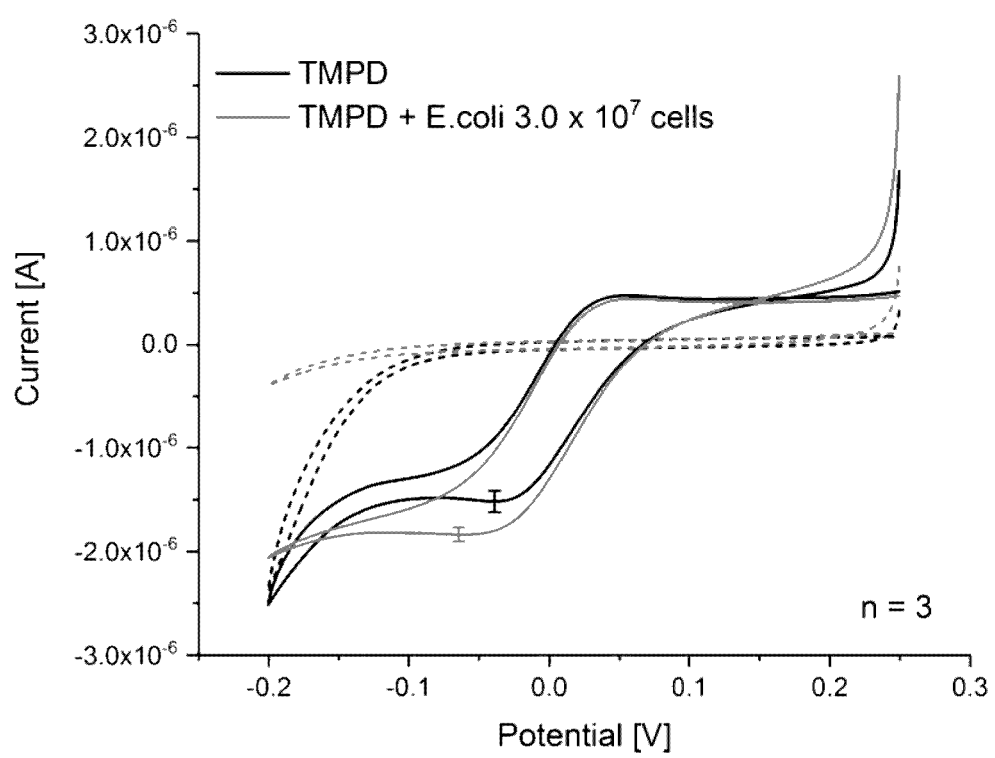

As during drop-casting both living and dead bacteria in a solution are deposited at an electrode, flow cytometry measurements were performed to estimate the percentage of living cells in solution that contribute to the electrochemical signal (FIG. 7). Analysis of B. subtilis revealed a cell viability of about 90%, whereas E. coli bacteria showed about 97% cell viability, which had to be respected for the calculation of a quantitative turnover number. Taking the electrochemical current during chronoamperometry (measurement point at 8 s), a turnover number was determined. At a bacteria count ranging from zero up to $10^7$, this turnover number was observed to scale linearly with the number of bacteria (FIG. 5c). As such, a turnover number per single bacterium ($T_{sb}$) could be calculated using the equation:

$$T_{sb} = \frac{\Delta I}{f N_{bac} e C} \quad (3)$$

in which ΔI is the difference in the magnitude of the current between the sample average (in the presence of the bacteria) and the control average (in the absence of the bacteria), e represents the charge ($1.60 \times 10^{-19}$ As), f is the viability factor (0.9 B. subtilis, 0.97 E. coli), $N_{bac}$ is the number of bacteria drop-cast onto the macroelectrode and C is the concentration of $TMPD^{+\bullet}$ in solution. For B. subtilis grown on agar, a $T_{sb}$ of 9.8 ($\pm 0.3$)$\times 10^8$ L mol$^{-1}$ s$^{-1}$ was calculated, whereas E. coli, grown to the exponential phase, revealed a $T_{sb}$ of 3.8 ($\pm 0.06$)$\times 10^8$ L mold s$^{-1}$, which corresponds to about 39% of the value obtained for B. subtilis. The analysis of TMPD oxidation by aerobic E. coli demonstrates the ability of electrochemistry to detect trace amounts of redox active species generated by biological matter. When grown in broth to the stationary phase, E. coli resulted in a $T_{sb}$ of 1.8 ($\pm 0.3$)$\times 10^9$ L mol$^{-1}$ s$^{-1}$, which represents an increase to about 185% compared to the value obtained for B. subtilis.

As a summary, FIG. 5c consolidates measurements in B. subtilis and E. coli under different growth conditions, representing the normalized current difference (current difference divided by the current recorded at the unmodified electrode) as a function of the number of bacteria immobilized at the macroelectrode. A linear relationship for currents obtained for samples containing up to $1 \times 10^7$ bacteria can be seen, before electrode blockage is observed at higher bacteria concentrations.

Thus, it has been demonstrated that the colorimetric oxidase test, commonly employed in cell and microbiology, can be transferred to an electrochemical set up and the expression of cytochrome c oxidase can be quantified in the model organism B. subtilis, resulting in a turnover number $T_{sb}$ of 9.8 ($\pm 0.3$)$\times 10^8$ L mol$^{-1}$ s$^{-1}$ for a single bacteria. Furthermore, although grown aerobically, E. coli bacteria show trace amounts of cytochrome c oxidase, the activity of which can be detected electrochemically, revealing a $T_{sb}$ of 3.8 ($\pm$0.06)$\times 10^8$ L mol$^{-1}$ s$^{-1}$ (about 39% compared to *B. subtilis*). The electrochemical recognition of the TMPD oxidation by bacterial oxidases can be applied to a variety of pathogens. Improving the experimental set up to lower the LOD to a competitive range and transferring the presented principle onto a selective device, the detection of pathogenic bacteria, such as *Neisseria meningitidis*, or bacteria related to sexually transmitted infections, is anticipated.

Supporting Information

Determination of Species Concentration

Concentrations of reduced and oxidized TMPD were determined by using the equation:

$$C = \frac{I_{ss}}{4FDa}$$

in which C is the concentration, $I_{ss}$ represents the steady state current, F is the Faraday constant, D is the diffusion coefficient and a is the radius of the electroactive surface of the microelectrode.

Determination of the TMPD-BF$_4$ Diffusion Coefficient

A diffusion coefficient ($D_{TMPD-BF_4}$) of $1 \times 10^{-5}$ cm$^2$ s$^{-1}$ was found following the reversible Randles-Ševčík method. Cyclic voltammetry in 2.1 mM TMPD-BF$_4$ in PBS buffer solution (pH 7.4) was performed using a 3 mm gold working electrode at scan rates ranging from 30 to 300 mV. A linear fit of the peak current values as a function of scan rate reveals a linear relationship with a slope of $1.3 \times 10^{-4}$ A s$^{1/2}$ V$^{-1/2}$. The diffusion coefficient was determined using the equation $$D = \left( \frac{m}{268600 \frac{As}{V^{1/2} \text{mol}} AC} \right)^2$$

in which D is the diffusion coefficient, m represents the slope, A is the electrode surface area, and C is the concentration.

Experimental Procedure for the Determination of Cell Viability

After harvesting, 1 ml bacteria suspension was transferred into an Eppendorf tube and stained with syto9 (1:1000) and propidium iodide (1:200) to gain information about live and dead cells in solution, respectively. Cells were incubated for 5 min at room temperature, followed by centrifugation for 3 min at 3000 rcf. Bacteria were resuspended in 1 mL PBS, followed by another centrifugation step for 3 min at 3000 rcf. Cells were resuspended in PBS and analysed using a BioRad S3e FACS instrument (standard configuration, 488 nm and 651 nm lasers, autogimbal 100 μm nozzle, BioRad, UK) and BioRad ProSort 1.5 software. The flow cytometric measurements are shown in FIG. 7.

REFERENCES MENTIONED HEREIN OR OTHERWISE USEFUL FOR BACKGROUND

K. L. Adams, M. Puchades, A. G. Ewing, In vitro electrochemistry of biological systems, Annu. Rev. Anal. Chem. 1 (2008) 329-355. doi:10.1146/annurev.anchem.1.031207.113038.

[2] D. Ivnitski, I. Abdel-Hamid, P. Atanasov, E. Wilkins, S. Stricker, Application of electrochemical biosensors for detection of food pathogenic bacteria, Electroanalysis. 12 (2000) 317-325. doi:10.1002/(SICI)1521-4109 (20000301)12:5<317::AID-ELAN317>3.0.CO;2-A.

[3] E. Y. Jomma, S.-N. Ding, Recent advances on electrochemical enzyme biosensors, Curr. Anal. Chem. 12 (2016) 5-21. https://www.scopus.com/inward/record.uri?eid=2-s2.0-84945358731&partnerID=40&md5=84b8271388d24c75bb89e156ef27aab2.

[4] C. Batchelor-McAuley, J. Ellison, K. Tschulik, P. L. Hurst, R. Boldt, R. G. Compton, In situ nanoparticle sizing with zeptomole sensitivity, Analyst. 140 (2015) 5048-5054. doi:10.1039/c5an00474h.

[5] L. Yang, R. Bashir, Electrical/electrochemical impedance for rapid detection of foodborne pathogenic bacteria, Biotechnol. Adv. 26 (2008) 135-150. doi:http://dx.doi.org/10.1016/j.biotechadv.2007.10.003.

[6] S. Bergner, P. Vatsyayan, F.-M. Matysik, Recent advances in high resolution scanning electrochemical microscopy of living cells—A review, Anal. Chim. Acta. 775 (2013) 1-13. http://www.scopus.com/inward/record.url?eid=2-52.0-84876468081&partnerID=40&md5=614b508977f731cede7d2b04969151bc.

[7] A. J. Bard, X. Li, W. Zhan, Chemically imaging living cells by scanning electrochemical microscopy, Biosens. Bioelectron. 22 (2006) 461-472. http://www.scopus.com/inward/record.url?eid=2-s2.0-33749256400&partnerID=40&md5=400cb234b42aec781662181c81e11389.

[8] A. Lehninger, D. Nelson, M. Cox, Lehninger Biochemie, 3rd edition, Springer-Verlag Berlin Heidelberg New York, 2001.

[9] M. Nebel, S. Grützke, N. Diab, A. Schulte, W. Schuhmann, Visualization of oxygen consumption of single living cells by scanning electrochemical microscopy: The influence of the faradaic tip reaction, Angew. Chemie—Int. Ed. 52 (2013) 6335-6338. doi:10.1002/anie.201301098.

[10] X. Li, J. Dunevall, A. G. Ewing, Quantitative Chemical Measurements of Vesicular Transmitters with Electrochemical Cytometry, Acc. Chem. Res. 49 (2016) 2347-2354. doi:10.1021/acs.accounts.6b00331.

[11] A. Yakushenko, E. Kätelhön, B. Wolfrum, Parallel On-Chip Analysis of Single Vesicle Neurotransmitter Release, Anal. Chem. 85 (2013) 5483-5490. doi:10.1021/ac4006183.

[12] S. Kuss, D. Polcari, M. Geissler, D. Brassard, J. Mauzeroll, Assessment of multidrug resistance on cell coculture patterns using scanning electrochemical microscopy, Proc. Natl. Acad. Sci. U.S.A 110 (2013) 9249-9254. http://www.scopus.com/inward/record.url?eid=2-s2.0-84878712878&partnerID=40&md5=d5970e4ce6fa38e52ed43116f04b1d44.

[13] C. Chan, L. Sepunaru, S. V Sokolov, E. Kätelhön, N. P. Young, R. G. Compton, Catalytic activity of catalase-silica nanoparticle hybrids: from ensemble to individual entity activity, Chem. Sci. 8 (2017) 2303-2308. doi:10.1039/c6sc04921d.

[14] J. Hagen, ed., Industrial Catalysis: A Practical Approach, 2nd ed., Wiley-VCH: Weinheim, 2006.

[15] G. N. Nobre, M. J. Charrua, M. M. Silva, The oxidase test in yeasts of medical importance, J. Med. Microbiol. 23 (1987) 359-361. http://jmm.microbiologyresearch.org/content/journal/jmm/10.1099/00222615-23-4-359.

[16] H. D. Isenberg, Clinical Microbiology Procedures Handbook, American Society for Microbiology, 2004.

[17] J. F. MacFaddin, Biochemical Tests for Identification of Medical Bacteria, 3rd ed., Lippincott Williams and Wilkins, 2000.

[18] L. Michaelis, M. P. Schubert, S. Granick, The Free Radicals of the Type of Wurster's Salts, J. Am. Chem. Soc. 61 (1939) 1981-1992. doi:10.1021/ja01877a013.

[19] D. Menshykau, I. Streeter, R. G. Compton, Influence of electrode roughness on cyclic voltammetry, J. Phys. Chem. C. 112 (2008) 14428-14438. doi:10.1021/jp8047423.

[20] J. F. MacFaddin, Biochemical tests for identification of medical bacteria, 3rd ed., Lippincott Williams & Wilkins, 2000.

[21] B. Alberts, A. Johnson, J. Lewis, M. Raff, K. Roberts, P. Walter, Molecular Biology of the Cell, 4th ed., Taylor & Francis Books, Inc., 2002.

[22] O. Tenaillon, D. Skurnik, B. Picard, E. Denamur, The population genetics of commensal *Escherichia coli*, Nat Rev Micro. 8 (2010) 207-217. http://dx.doi.org/10.1038/nrmicro2298.

[23] J. Gordon, J. W. McLeod, The practical application of the direct oxidase reaction in bacteriology, J. Pathol. Bacteriol. 31 (1928) 185-190. doi:10.1002/path.1700310206.

[24] J. Yamauchi, H. Fujita, Magnetic study of N,N,N',N'-tetramethyl-phenylene diamine (Wurster's Blue) Iodide cation radical, Bull. Chem. Soc. Jpn. 63 (1990) 2928-2932. doi:10.1246/bcsj.63.2928.

[25] D. A. C. Brownson, C. E. Banks, Interpreting Electrochemistry, in: Handb. Graphene Electrochem., Springer-Verlag London Ltd., London, 2014.

[26] M. Rudolph, A fast implicit finite difference algorithm for the digital simulation of electrochemical processes, J. Electroanal. Chem. Interfacial Electrochem. 314 (1991) 13-22. doi:http://dx.doi.org/10.1016/0022-0728(91)85425-O.

[27] M. Rudolph, Digital simulations with the fast implicit finite difference (FIFD) algorithm: Part II. An improved treatment of electrochemical mechanisms with second-order reactions, J. Electroanal. Chem. 338 (1992) 85-98. doi:http://dx.doi.org/10.1016/0022-0728(92)80415-Z.

[28] M. Rudolph, Digital simulations with the fast implicit finite-difference (FIFD) algorithm. part 4. Simulation of electrical migration and diffuse double-layer effects, J. Electroanal. Chem. 375 (1994) 89-99. doi:http://dx.doi.org/10.1016/0022-0728(94)03404-4.

[29] M. Rudolph, D. P. Reddy, S. W. Feldberg, A Simulator for Cyclic Voltammetric Responses, Anal. Chem. 66 (1994) 589A-600A. https://www.scopus.com/inward/record.uri?eid=2-s2.0-0028441766&partnerID=40&md5=60ab74ad03fd5107f1745979c46e23a0.

[30] M. Rudolph, Digital Simulations with the Fast Implicit Finite Difference Algorithm: The Development of a General Simulator for Electrochemical Processes, in: I. Rubinstein (Ed.), Phys. Electrochem. Princ. Methods Appl., Marcel Dekker, Ney York, 1995.

[31] S. Kuss, R. G. Compton, Electrocatalytic detection of ascorbic acid using N,N,N',N'-tetramethyl-para-phenylene-diamine (TMPD) mediated oxidation at unmodified gold electrodes; reaction mechanism and analytical application, Electrochim. Acta. 242 (2017). doi:10.1016/j.electacta.2017.05.003.

[32] L. Thony-Meyer, F. Fischer, P. Kunzler, D. Ritz, H. Hennecke, *Escherichia coli* genes required for cytochrome c maturation, J. Bacteriol. 177 (1995) 4321-4326. https://www.scopus.com/inward/record.uri?eid=2-52.0-0029080566&partnerID=40&md5=8fbcb6ec09880195122ebae76f411a2a.

[33] C. Iobbi-Nivol, H. Crooke, L. Griffiths, J. Grove, H. Hussain, J. Pommier, V. Mejean, J. A. Cole, A reassessment of the range of c-type cytochromes synthesized by *Escherichia coli* K-12, FEMS Microbiol. Lett. 119 (1994) 89-94. doi:http://dx.doi.org/.

[34] J. S. Chang, T. Wendt, W. Qu, L. Kong, Y. S. Zou, A. M. Schmidt, S.-F. Yan, Oxygen Deprivation Triggers Upregulation of Early Growth Response-1 by the Receptor for Advanced Glycation End Products, Circ. Res. 102 (2008) 905 LP-913. http://circres.ahajournals.org/content/102/8/905.abstract.

[35] C. von Wachenfeldt, L. Hederstedt, *Bacillus subtilis* holo-cytochrome c-550 can be synthesised in aerobic *Escherichia coli*, FEBS Lett. 270 (1990) 147-151. doi:10.1016/0014-5793(90)81255-M.

[36] Agilent Technologies, *E. coli* Cell Culture Concentration from OD600, (2017). http://www.genomics.agilent.com/biocalculators/calcODBacterial.jsp (accessed Jun. 1, 2017).

[37] A. J. Fisher, T. N. Rosenstiel, M. C. Shirk, R. Fall, Nonradioactive assay for cellular dimethylallyl diphosphate, Anal. Biochem. 292 (2001) 272-279. doi:10.1006/abio.2001.5079.

[38] M. C. Arrieta, B. K. Leskiw, W. R. Kaufman, Antimicrobial activity in the egg wax of the African cattle tick *Amblyomma hebraeum* (Acari: Ixodidae), Exp. Appl. Acarol. 39 (2006) 297-313. doi:10.1007/s10493-006-9014-5.

[39] T. J. Cardwell, J. Mocak, J. H. Santos, A. M. Bond, Preparation of microelectrodes: Comparison of polishing procedures by statistical analysis of voltammetric data, Analyst. 121 (1996) 357-362. doi:10.1039/an9962100357.

Example 2

Chemical Reagents

All chemicals were purchased from Sigma-Aldrich, if not indicated otherwise. Phosphate buffered saline (PBS, 0.17 M) solution consists of 8 g sodium chloride (≥99%), 0.2 g potassium chloride (≥99%). 1.44 g sodium phosphate dibasic (99%), 0.24 g potassium phosphate dibasic (≥99%) and was completed to 1 L using nanopure water with a resistivity not less than 18.2 MO cm at 25° C. (Millipore water purification system).

Self-Assembled Monolayer Formation

Figures 9A, 9B, 9C, 9D, 9E:
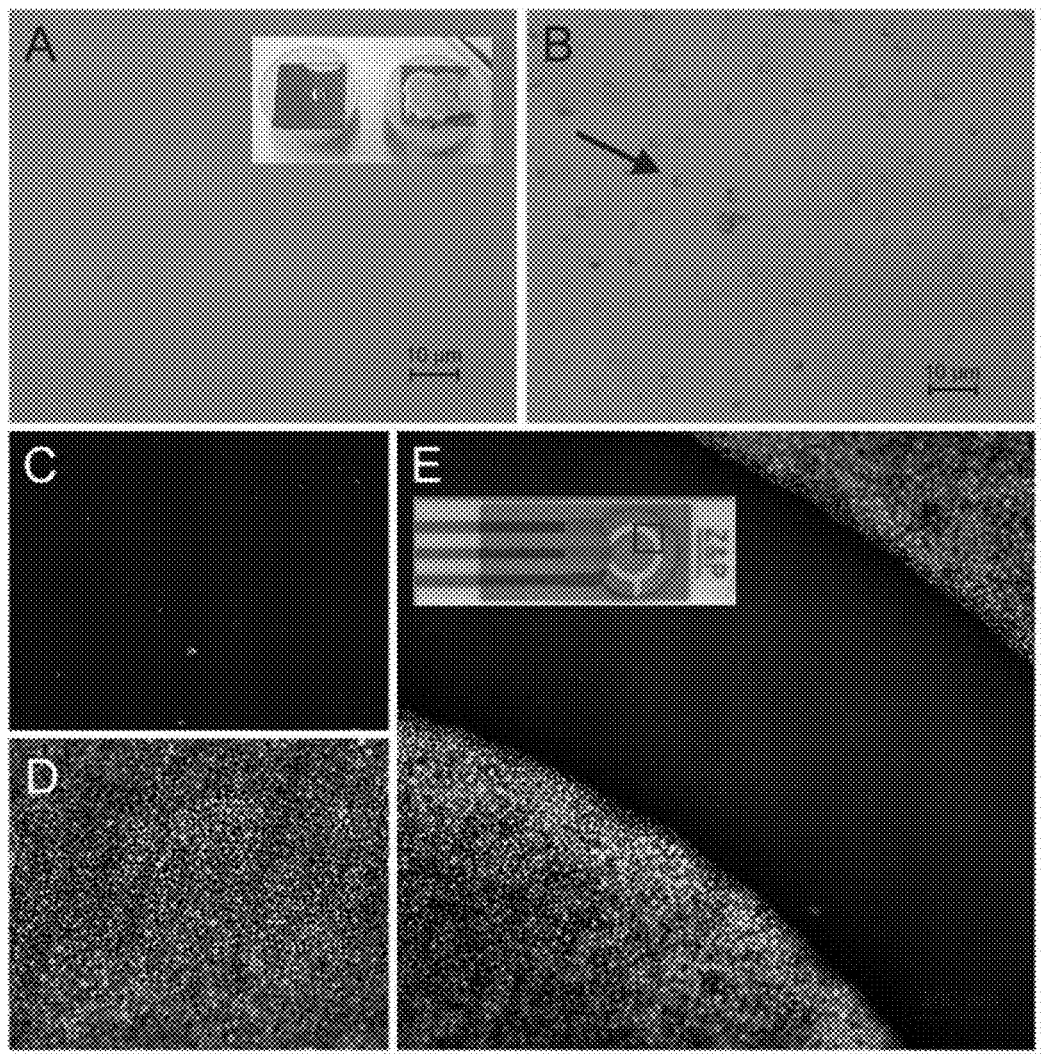
FIGS. 9A to 9E show SEM micrographs of the surface modification of gold substrates and electrodes; in particular.
Figure 10:
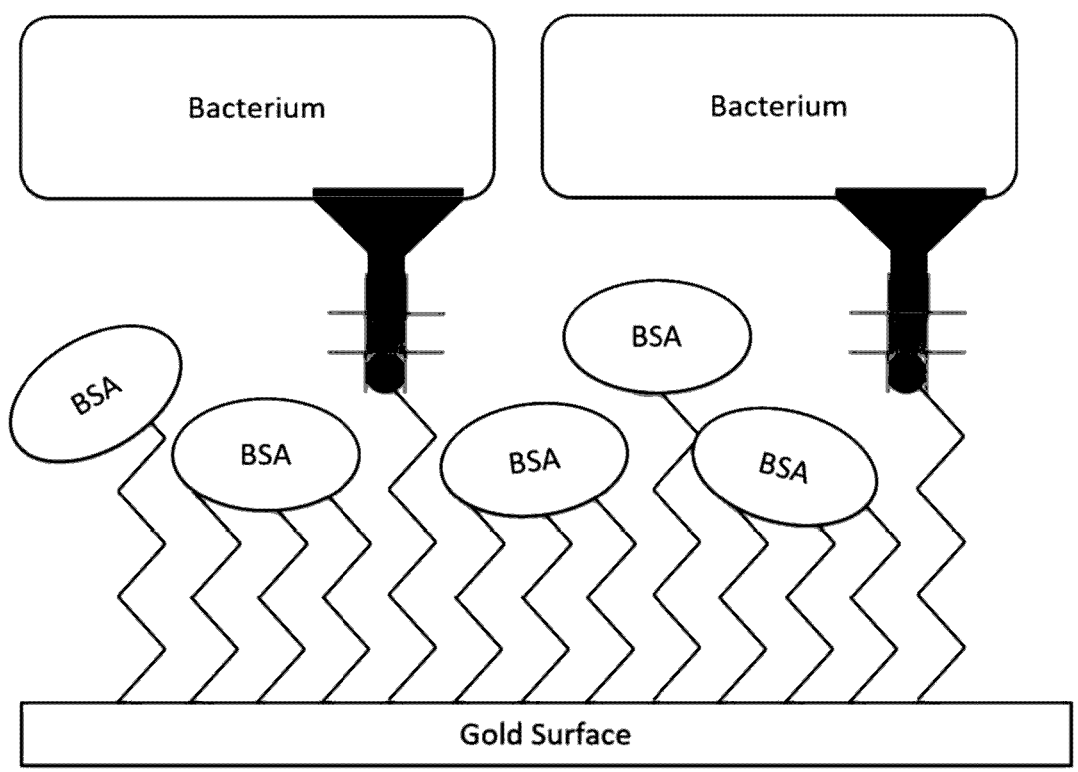

Self-assembled monolayers (SAMs) were constructed following the protocol of Maalouf et al. [1] All washing steps were carried out in nanopure $H_2O$ by carefully dipping the modified electrodes or SPE sensors into H2O ten times. In short, electrodes or SPE sensors were exposed for 24 hr at 25° C. to an ethanol-chloroform mix (1:1), containing 0.2 mM HSCH2[CH2]9CH2NHCOBiotin (biotin-thiol) and 0.8 mM octanethiol (spacer). After washing, the modified sensors were incubated in 1 µM bovine serum albumin for 30 min to block any unspecific binding sites. Sensors were washed and incubated for 45 min in 10 µM neutravidin and washed again. Sensors were exposed to specific biotinylated polyclonal antibodies against either *E. coli* (dilution 1:200) or *N. gonorrhea* (dilution 1:250) in PBS for one hr. After another washing step, sensors were exposed for 45 min to 1 hr to bacteria solutions at various concentrations or PBS as control. Optical micrographs showing successful SAMs on gold are presented in FIG. 9 and a schematic representation of the procedure summary is shown in FIG. 10.

Bioelectrochemical Measurements

Electrochemical measurements were carried out using a modular potentiostat (PGSTAT302N, Autolab, UK). All experiments involving bacteria cultures were conducted at 37° C. inside a Faraday cage. An in-house fabricated gold microelectrode with a diameter of 6.9 mm was employed to determine the concentration of TMPD-BF4 in solution by cyclic voltammetry. Information about calculations can be found in Kuss et al. [2] A 2 mm (diameter) gold macroelectrode (Alvatek Ltd, UK) was used as working electrode for bioelectrochemical measurements. The working electrode was polished prior to experiments using a water-alumina mix (1.0, 0.3 and 0.05 mm, 30 seconds for each grade) on microcloth polishing pads (Buehler, USA). [3] In all experiments, a standard calomel electrode and a platinum mesh were employed as reference and counter electrodes, respectively. After polishing, sonication of the macroelectrode was applied for 2 minutes to assure removal of alumina powder from the electrode surface. To dropcast $Alcaligenes\ faecalis$ bacteria, the macroelectrode was placed in an electrode holder inside a 50 mL falcon tube, keeping it in upright position. After deposition of 3 μl ($1.0 \times 10^7$ cells) of bacteria suspension the falcon tube was closed and bacteria suspension dried under $N_2$ flow. Evaporation was monitored by eye and $N_2$ flow was stopped the moment all liquid was evaporated. The electrode was removed from the holder and was placed in the electrochemical set up. The electrochemical cell remained thermostatted to 37° C. throughout the experiments.

Screen printed electrodes were provided by Zimmer&Peacock and did not require polishing prior to experiments. Chronoamperometry was carried out immediately after dropcasting or immobilization of bacteria to minimize cell death at the electrode. For all organisms, a delay time of 45 s was applied after the electrode/SPE sensor was brought in contact with the solution, holding the electrode at open circuit potential. An oxidative potential of 250 mV was applied for 5 s, followed by a potential step to a reductive regime of −150 mV, which was held for 5 s also. All potentials are indicated vs. a saturated calomel reference electrode (SCE).

FIGS. 11 to 20 show results of tests carried out.

Figure 11:
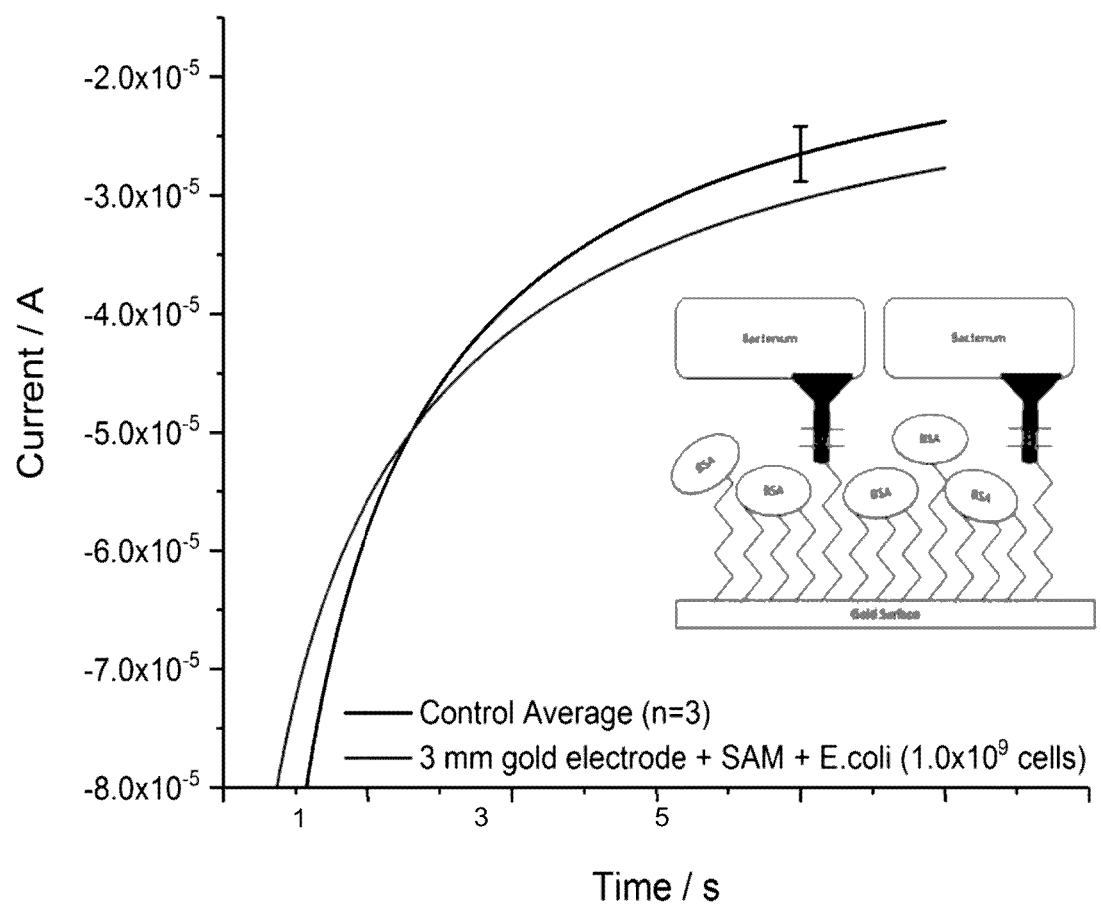

FIG. 11 shows the detection of $E.\ coli$ at functionalized macroelectrodes. An electrochemical current increase is observed following the binding of $E.\ coli$ to a fully functionalized macroelectrode (grey), compared to a bare electrode (black). The error bar is representing three times the standard deviation.

Figure 12:
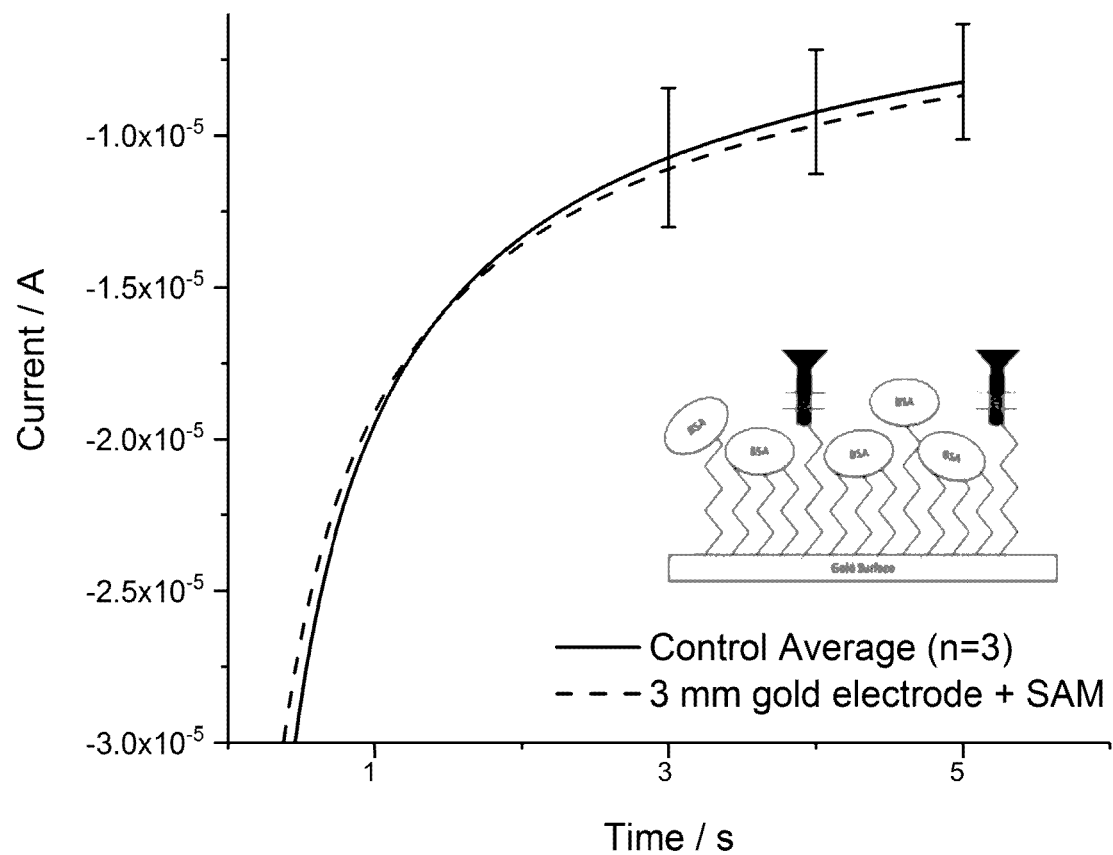

FIG. 12 shows a negative control at a functionalized macroelectrode. No increase in electrochemical current is observed at the electrode in the absence of $E.\ coli$ bacteria (dotted line), compared to a bare electrode (full line). Error bars are representing three times the standard deviation.

Figure 13:
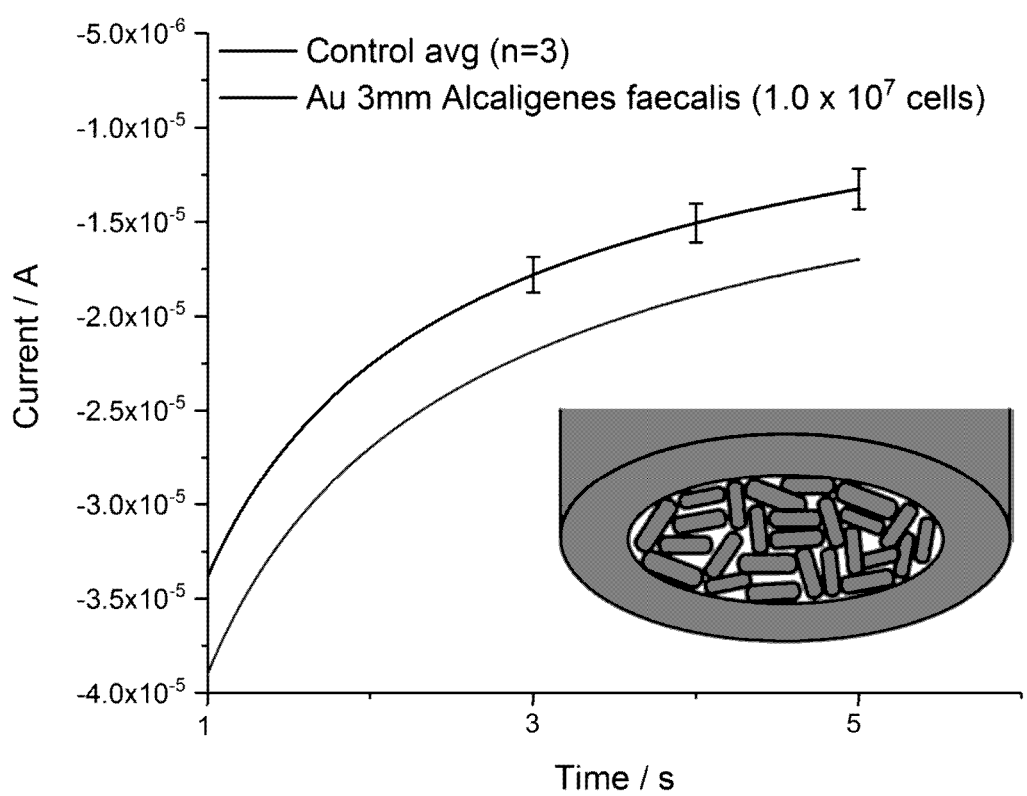

FIG. 13 shows the detection of $A.\ faecalis$ at a macroelectrodes. Dropcasted $A.\ faecalis$ are detected at a macroelectrode, as the electrochemical current increases significantly (grey). Error bars are representing three times the standard deviation.

Figure 14:
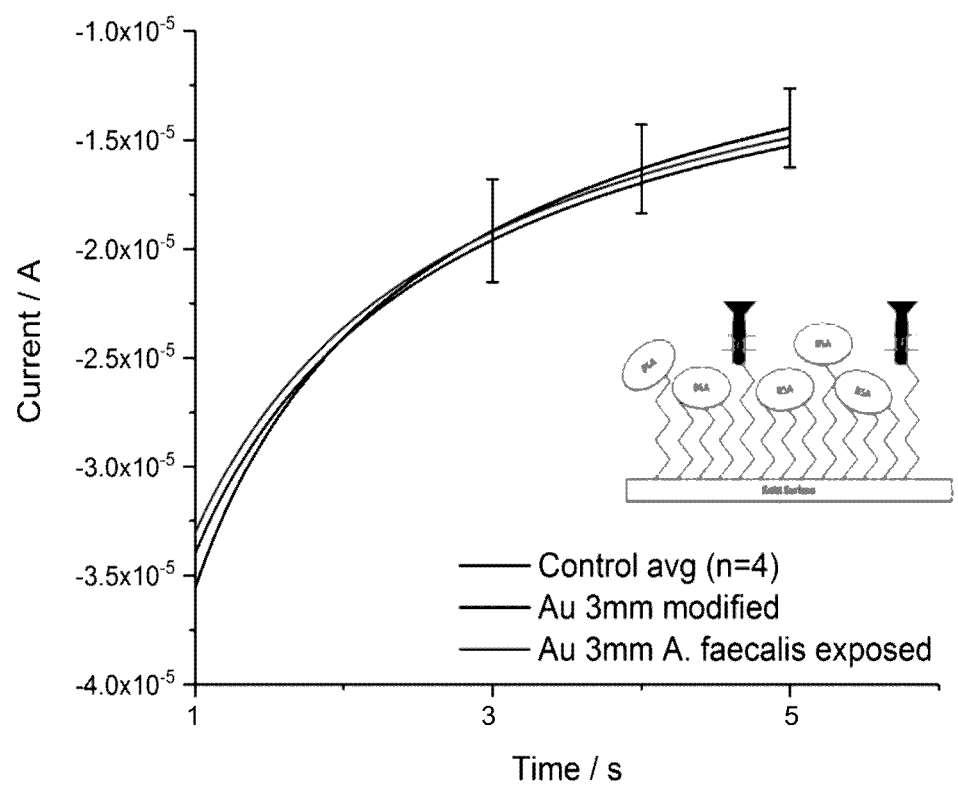

FIG. 14 shows a negative control in the presence of $A.\ faecalis$ at a macroelectrodes. The exposure of $A.\ faecalis$ to a fully functionalized macroelectrode, containing an anti-$E.\ coli$ antibody does not result in an increase of the electrochemical current (grey), which cannot be distinguished from the signal obtained at control electrodes (black=bare electrode, dark grey=modified electrode in the absence of bacteria). Error bars are representing three times the standard deviation.

Figure 15:
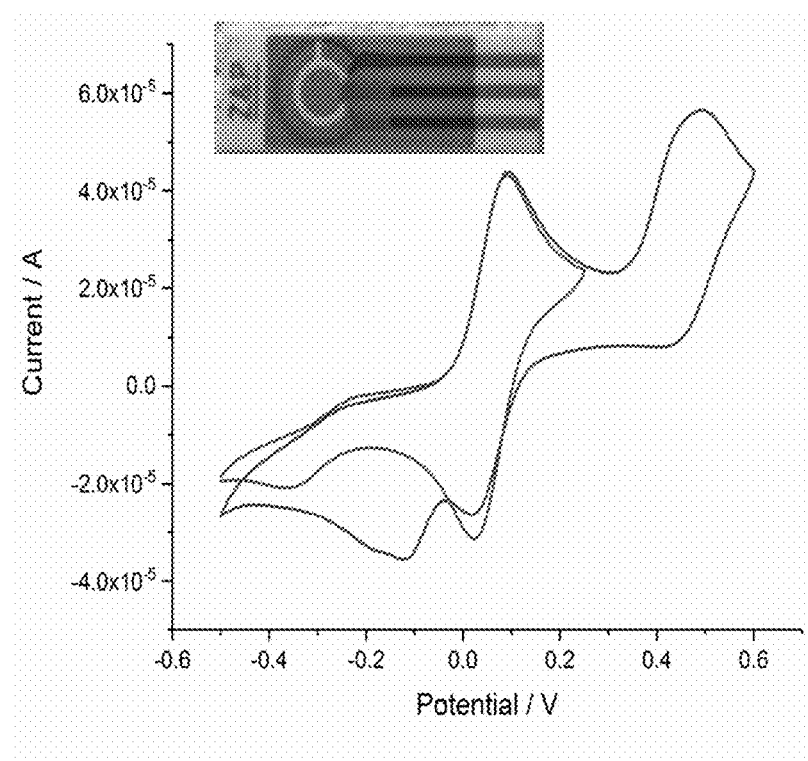

FIG. 15 shows the electrochemistry of TMPD at SPEs provided by Zimmer&Peacock.

Figure 16:
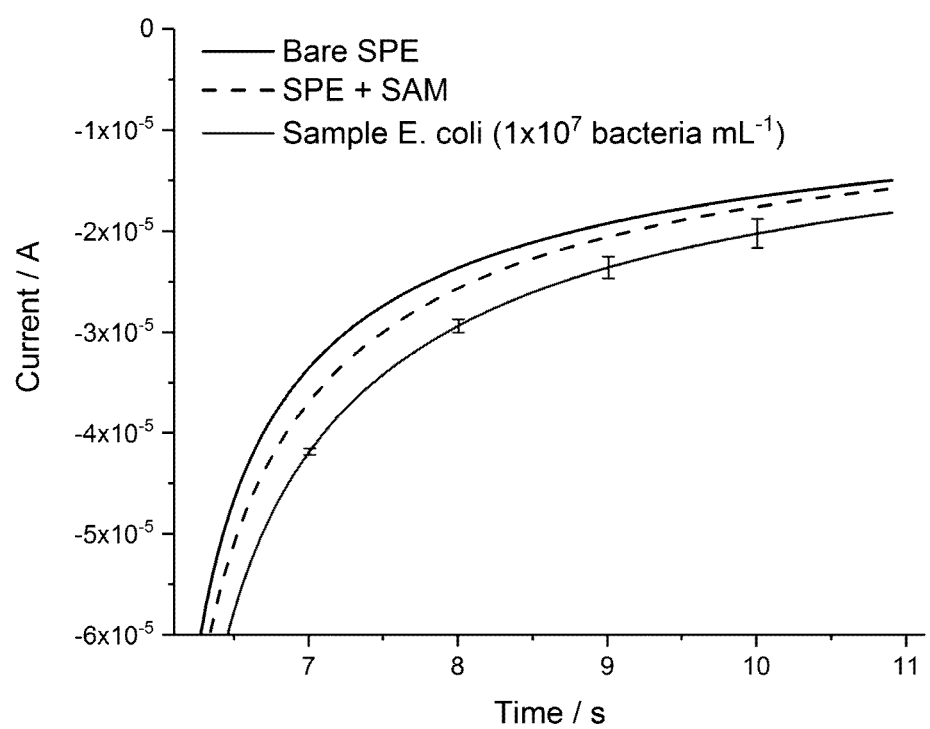

FIG. 16 shows the detection of $N.\ gonorrhoea$ at functionalized SPEs, containing an anti-$N.\ gonorrhoea$ antibody. Immobilized $N.\ gonorrhoea$ bacteria result in a significantly enhanced electrochemical current (grey), in contrast to a blank electrode (black, full line) and a functionalized sensor, in the absence of bacteria (black, dotted line). Error bars are representing three times the standard deviation.

Figure 17:
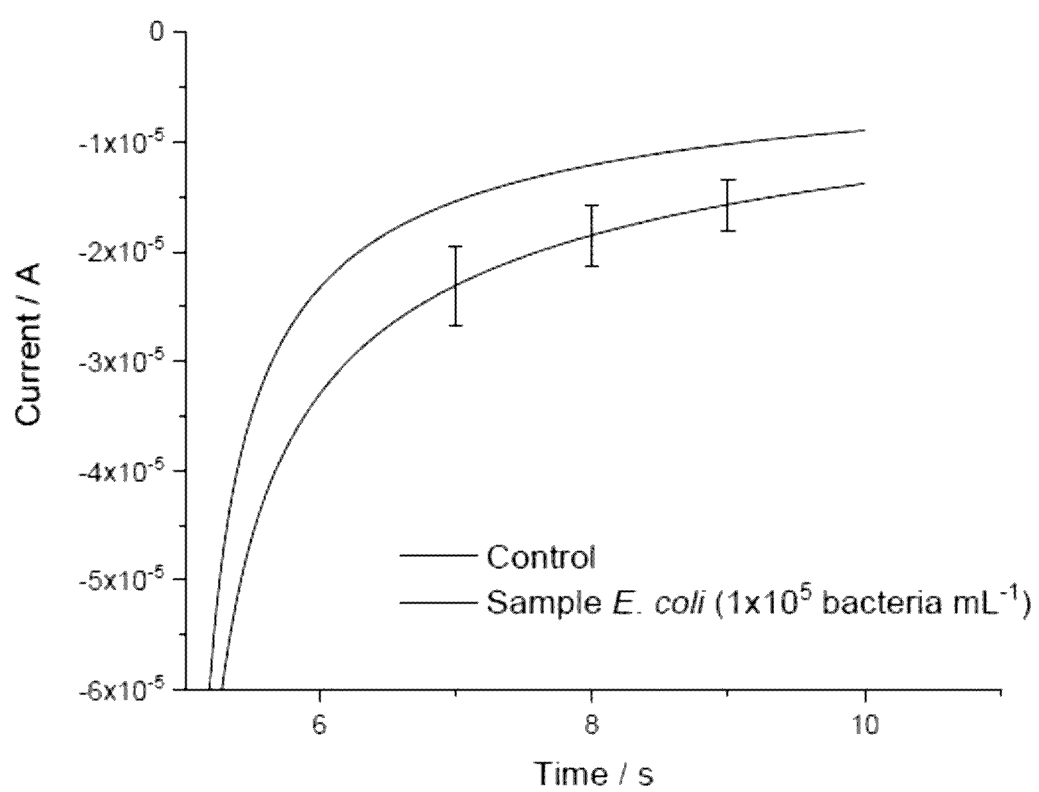

FIG. 17 shows the detection of $E.\ coli$ at functionalized SPEs containing an anti-$E.\ coli$ antibody. Immobilized $E.\ coli$ bacteria result in a significantly enhanced electrochemical current (grey), in contrast to the control, in the absence of bacteria (black). Error bars are representing three times the standard deviation.

Figure 18:
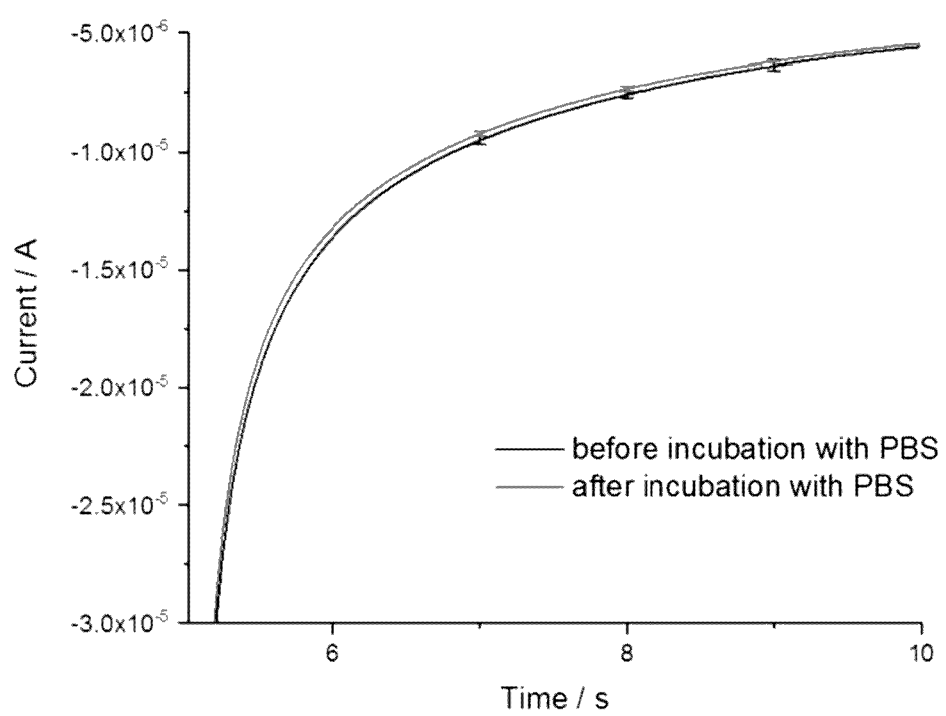

FIG. 18 shows PBS control experiment for a single functionalized SPEs containing an anti-$E.\ coli$ antibody. No significant change in current is observed after a 1 hour incubation of the sensor in PBS. Error bars are representing three times the standard deviation.

Figure 19:
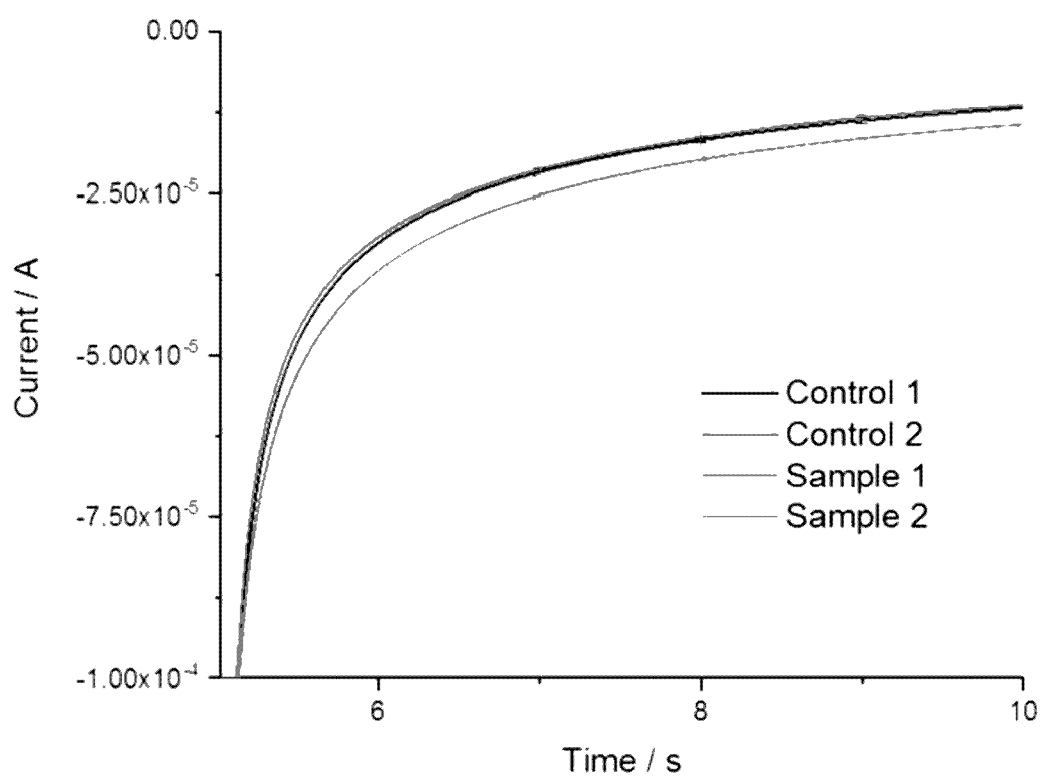

FIG. 19 shows the detection of $E.\ coli$ at single functionalized SPEs containing an anti-$E.\ coli$ antibody. Controls showing fully functionalized sensors before incubation with bacteria (black lines). After one hour of sensor incubation in bacteria suspension, immobilized $E.\ coli$ bacteria result in a significantly enhanced electrochemical current (grey lines). Error bars are representing three times the standard deviation.

Figure 20:
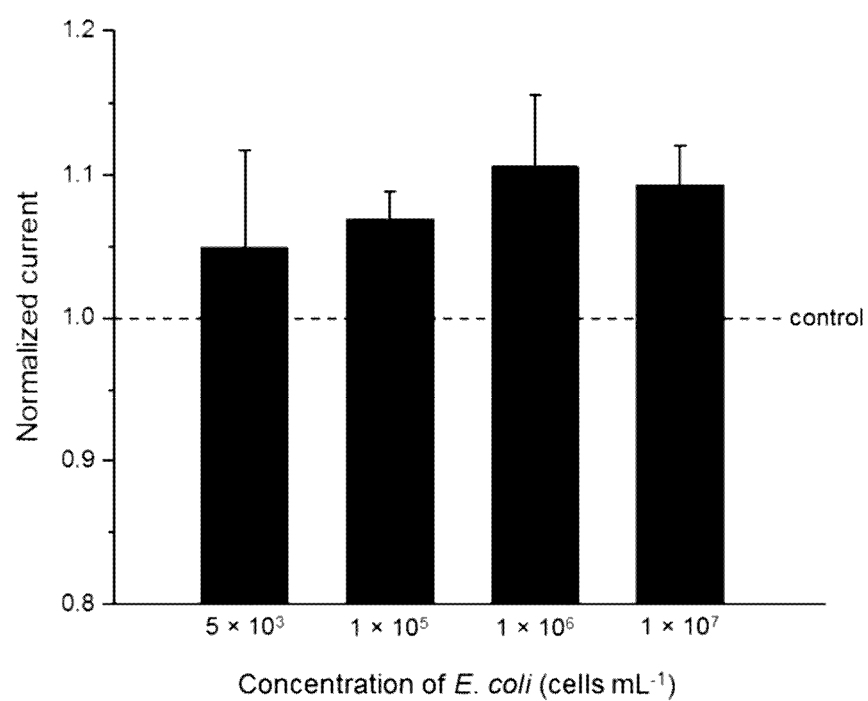

FIG. 20 shows the detection of $E.\ coli$ at functionalized SPEs containing an anti-$E.\ coli$ antibody at different concentrations. Immobilized $E.\ coli$ bacteria result in a significantly enhanced electrochemical current, in contrast to the control, in the absence of bacteria (dotted line). Error bars are representing three times the standard deviation.

REFERENCES MENTIONED IN EXAMPLE 2

1. Maalouf, R., et al., Label-Free Detection of Bacteria by Electrochemical Impedance Spectroscopy: Comparison to Surface Plasmon Resonance. Analytical Chemistry, 2007. 79(13): p. 4879-4886.
2. Kuss, S., et al., Electrochemical recognition and quantification of cytochrome c expression in: $Bacillus\ subtilis$ and aerobe/anaerobe $Escherichia\ coli$ using N, N, N', N'-tetramethyl-para-phenylene-diamine (TMPD). Chemical Science, 2017. 8(11): p. 7682-7688.
3. Cardwell, T. J., et al., Preparation of microelectrodes: Comparison of polishing procedures by statistical analysis of voltammetric data. Analyst, 1996. 121(3): p. 357-362.

The invention claimed is:
1. A method of determining the presence of bacteria expressing cytochrome c oxidase ('the bacteria'), the method comprising:
providing a liquid sample suspected of containing the bacteria;
providing a compound that has two redox states: a reduced state and an oxidised state, wherein cytochrome c oxidase can convert the compound from its reduced state to its oxidised state;

contacting an electrode either with
(i) the compound in its oxidised state in the presence of the liquid sample, then applying a reductive potential and measuring the current at the electrode; or
(ii) the compound in its reduced state in the presence of the liquid sample, then applying an oxidative potential and measuring the current at the electrode; and
comparing the magnitude of the current produced by the reductive potential or oxidative potential in the presence of the liquid sample suspected of containing the bacteria with the magnitude of the current produced under the same conditions, but in the absence of the liquid sample suspected of containing the bacteria,
wherein a difference between the magnitude of current produced in the presence of the liquid sample suspected of containing the bacteria and the magnitude of current produced in the absence of the liquid sample suspected of containing the bacteria indicates the presence of the bacteria.

2. The method according to claim 1, wherein the compound is provided as a mixture of the compound in the oxidised state and the compound in the reduced state and
in (i) involves before applying the reductive potential, applying an oxidative potential to convert at least some of, optionally all of, the compound in its reduced state to the compound in its oxidised state; or
in (ii) involves before applying the oxidative potential, applying a reductive potential to convert at least some of, optionally all of, the compound in its oxidised state to the compound in its reduced state.

3. The method according to claim 1, wherein the electrode is contacted with the compound in its oxidised state, and a higher magnitude of current is produced in the presence of the liquid sample suspected of containing the bacteria than in the absence of the liquid sample suspected of containing the bacteria.

4. The method according to claim 1, wherein the electrode is contacted with the compound in its reduced state, and a lower magnitude of current is produced in the presence of the liquid sample suspected of containing the bacteria than in the absence of the liquid sample suspected of containing the bacteria.

5. The method according to claim 1, wherein the bacteria is selected from *Bacillus* bacteria, *Neisseria* bacteria, Pseudomonadaceae bacteria, *Campylobacter* bacteria, *Pasteurella* bacteria, *Alcaligens* bacteria, *Aeromonas* bacteria, *Vibrio* bacteria, *Brucella* bacteria, *Helicobacter* bacteria, *Haemophilus* bacteria, *Moraxella* bacteria, *Legionella pneumophila* bacteria *Chlamydia trachomatis* bacteria, *Streptococcus* bacteria, *Staphylococcus* bacteria, *Listeria* bacteria, *Mycobacterium tuberculosis* bacteria, *Escherichia coli* bacteria and *Alcaligenes* bacteria.

6. The method according to claim 1, wherein the current is measured by cyclic voltammetry or chronoamperometry.

7. The method according to claim 1, wherein the liquid sample suspected of containing the bacteria is provided less than 3 minutes before the current is measured.

8. The method according to claim 1, wherein the liquid sample suspected of containing the bacteria is on a surface of the electrode.

9. The method according to claim 1, wherein the compound is in solution in a carrier medium.

10. The method according to claim 1, wherein the compound has a standard electrode potential of between −0.5 V and 0.5 V, vs SCE.

11. The method according to claim 1, wherein the compound is selected from a phenylene diamine, a polyphenol and a hydroquinone.

12. The method according to claim 11, wherein the phenylene diamine has the following structure:

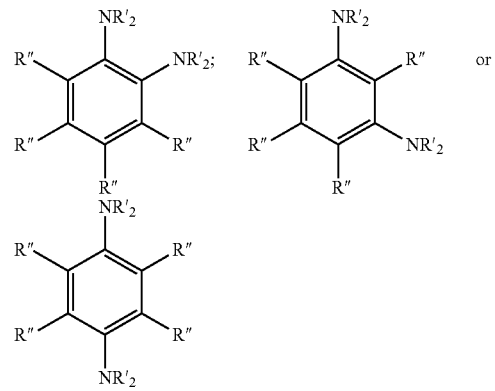

in which
each R' is independently selected from hydrogen, alkyl, or alkenyl; and
each R" is independently selected from hydrogen, alkyl, or alkenyl.

13. The method according to claim 11, wherein the phenylene diamine is a nitrogen-substituted phenylene diamine.

14. The method according to claim 11, wherein the compound is selected from N,N,N',N'-tetramethyl-para-phenylene diamine, N,N,N',N'-tetramethyl-para-phenylene diamine dihydrochloride, N,N,N',N'-tetramethyl-para-phenylene diamine tetrafluoroborate, N,N-dimethyl-para-phenylene diamine, N,N-dimethyl-para-phenylene diamine dihydrochloride, N,N-dimethyl-para-phenylenediamine oxalate, para-aminodimethylaniline.

15. The method according to claim 1, wherein if it is determined that the liquid sample contains the bacteria and the bacteria is identified, the method further comprises determining the number of bacteria present by comparing the normalised current difference to a calibration curve in which the normalized current difference for the bacteria has been plotted against the number of bacteria in several calibration liquid samples.

16. The method according to claim 1, wherein if it is determined that the liquid sample contains the bacteria and the bacteria is identified, the method further comprises determining the number of bacteria in the liquid sample (N) by using the following equation:

$$N = \frac{\Delta I}{T_{sb} f e C}$$

in which
$\Delta I$ is the difference between the magnitude of current produced in the presence of the liquid sample containing the bacteria and the magnitude of current produced in the absence of the liquid sample containing the bacteria;

$T_{sb}$ is the turnover number per single bacteria;
f is the viability factor for the bacteria;
e is the charge of an electron ($1.6 \times 10^{-19}$ As); and
C is the concentration of the compound.

17. An electrochemical sensor for determining the presence of bacteria expressing cytochrome c oxidase ('the bacteria') in a liquid sample suspected of containing the bacteria, the sensor comprising:
   an electrode; and
   a compound that has two redox states: a reduced state and an oxidised state, wherein cytochrome c oxidase can convert the compound from its reduced state to its oxidised state; and
   the sensor is adapted to:
   contact the electrode with a liquid sample suspected of containing the bacteria and either with
   (i) the compound in its oxidised state, then apply a reductive potential and measure the current at the electrode; or
   (ii) the compound in its reduced state, then apply an oxidative potential and measure the current at the electrode; and
   compare the magnitude of the current produced by the reductive potential or oxidative potential in the presence of the liquid sample suspected of containing the bacteria with the magnitude of the current produced under the same conditions, but in the absence of the liquid sample suspected of containing the bacteria,
   wherein a difference between the magnitude of current produced in the presence of the liquid sample suspected of containing the bacteria and the magnitude of current produced in the absence of the liquid sample suspected of containing the bacteria indicates the presence of the bacteria.

18. The electrochemical sensor according to claim 17, wherein the compound is a mixture of the compound in the oxidised state and the compound in the reduced state and
   (i) involves before applying the reductive potential, applying an oxidative potential to convert at least some of, optionally all of, the compound in its reduced state to the compound in its oxidised state; and
   (ii) involves before applying the oxidative potential, applying a reductive potential to convert at least some of, optionally all of, the compound in its oxidised state to the compound in its reduced state.

19. The electrochemical sensor according to claim 17, wherein the electrode is contacted with the compound in its oxidised state, and a higher magnitude of current is produced in the presence of the liquid sample suspected of containing the bacteria than in the absence of the liquid sample suspected of containing the bacteria.

20. The electrochemical sensor according to claim 17, wherein the electrode is contacted with the compound in its reduced state, and a lower magnitude of current is produced in the presence of the liquid sample suspected of containing the bacteria than in the absence of the liquid sample suspected of containing the bacteria.

* * * * *